United States Patent [19]

Abe et al.

[11] Patent Number: 5,168,100

[45] Date of Patent: Dec. 1, 1992

[54] HP530 COMPOUNDS AND PROCESS FOR PREPARING THE SAME

[75] Inventors: Naoki Abe; Nobuyasu Enoki; Yasukazu Nakakita; Hideaki Uchida; Ryoichi Sato; Suguru Takeo; Nobuhiro Watanabe, all of Yaizu, Japan

[73] Assignee: Sapporo Breweries Limited, Tokyo, Japan

[21] Appl. No.: 668,207

[22] Filed: Mar. 12, 1991

[30] Foreign Application Priority Data

| Mar. 16, 1990 | [JP] | Japan | 2-64008 |
| Aug. 9, 1990 | [JP] | Japan | 2-209310 |
| Nov. 29, 1990 | [JP] | Japan | 2-325867 |
| Nov. 29, 1990 | [JP] | Japan | 2-325868 |

[51] Int. Cl.$^5$ .................. A61K 31/35; C07D 311/78
[52] U.S. Cl. .............................. 514/453; 549/384
[58] Field of Search .................... 549/384; 514/453

[56] References Cited

U.S. PATENT DOCUMENTS 4,954,641  9/1990  Sato et al. .................. 549/384

FOREIGN PATENT DOCUMENTS 200818  11/1986  European Pat. Off. .
326173   8/1989  European Pat. Off. .
361510   4/1990  European Pat. Off. .
9009435  8/1990  World Int. Prop. O. .

OTHER PUBLICATIONS

The Journal of Antibiotics, vol. 42, No. 1, 149-153, (1989), "Ankinomycin, a Potent Antitumor Antibiotic".
The Journal of Antibiotics, vol. 42, No. 10, 1518-1519, (1989), "Antitumor Activity of Ankinomycin".

Primary Examiner—Nicky Chan
Attorney, Agent, or Firm—Oblon, Spivak, McClelland, Maier & Neustadt

[57] ABSTRACT

Disclosed are novel HP530 compounds, their derivatives or their pharmaceutically permissible salts, a process for preparing them and an antitumor substances containing them as active ingredient. The HP530 compounds and their derivatives expressed by the general formula below can be prepared by cultivating Streptomyces sp. HP530 (FERM BP-2786) or and chemically derivation.

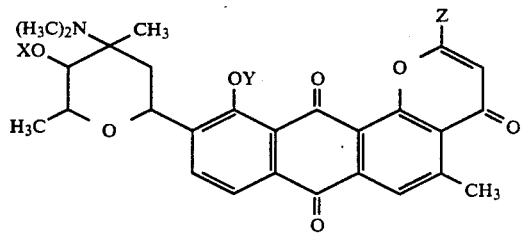

where X is a $C_2-C_4$ acyl group or a hydrogen atom, Y is a $C_2-C_4$ acyl group or a hydrogen atom and Z is a group expressed by the formula (II), (III) or (IV).

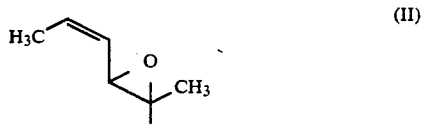

(II)

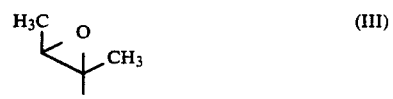

(III)

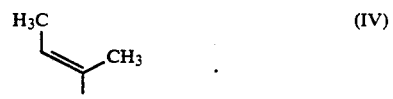

(IV)

10 Claims, 18 Drawing Sheets

WAVE LENGTH (nm)

WAVE LENGTH (nm)

HP530 COMPOUNDS AND PROCESS FOR PREPARING THE SAME

BACKGROUND OF THE INVENTION

1. Field of the Invention

This invention relates to novel antitumor compounds of HP530 or their pharmaceutically permissible salts, processes for preparing them and antitumor compounds containing the HP530 compounds as their active ingredient.

2. Description of the Prior Art

Microorganisms are known to produce a variety of antitumor compounds having the features in their chemical structures in a broad range. Antitumor compounds belonging to the pluramycin group exhibiting a strong antitumor effect have been reported in some papers as, for example, pluramycin A (The Journal of Antibiotics, Series A, Vol. 9, pp. 75, 1956), neopluramycin (The Journal of Antibiotics, Vol. 23, pp. 354, 1970; Vol. 30, pp. 1143, 1977), kidamycin (The Journal of Antibiotics, Vol. 24, pp. 599, 1971), hedamycin (Helvetica Chimica Acta, Vol. 60, pp. 896, 1971), rubiflavins (Helvetica Chimica Acta, Vol. 63, pp. 2446, 1980; Vol. 70, pp. 1217, 1987), SS21020 compounds(Japanese Patent Kokai Koho No. 277682/1986), ankinomycin (The Journal of Antibiotics, Vol. 42, pp. 149; 1989), altromycin (The Journal of Antibiotics, Vol. 43, pp. 223, 1990), DC92-B (The Journal of Antibiotics, Vol. 43, pp. 485, 1990), and so forth.

Besides their peculiar activity, however, the conventional antitumor compounds involve generally the common problem in that they exhibit strong toxicity.

SUMMARY OF THE INVENTION

It is therefore an object of the present invention to provide a novel antitumor compound which can be a more effective medicine than the heretofore known antitumor compounds and also to provide the process for producing such compounds in order to solve the problem described above.

DETAILED DESCRIPTION OF THE PREFERRED EMBODIMENTS

Figure 1:
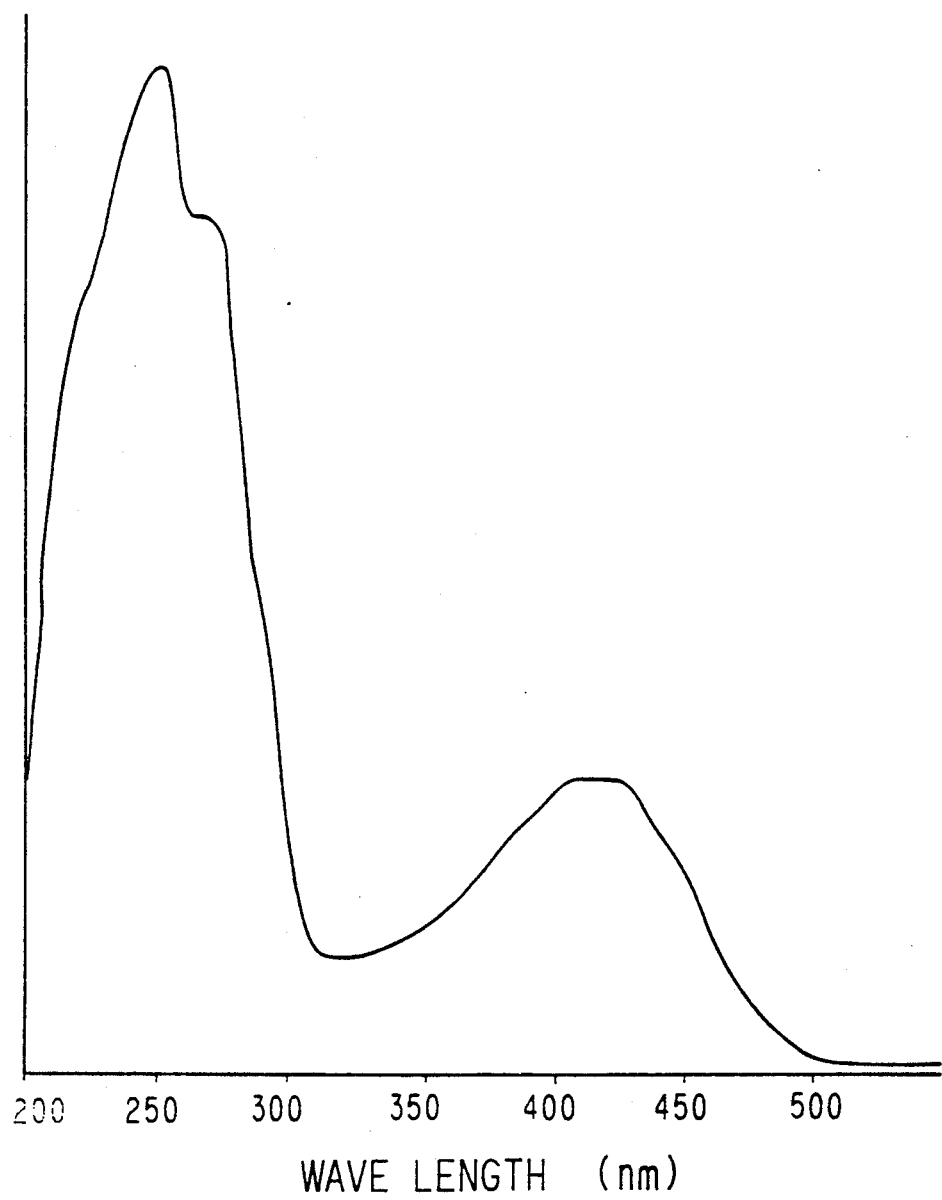
FIG. 1 is a ultraviolet absorption spectrum of HP530D in a methanol solution.

In order to solve the problem described above, the inventors of the present invention isolated a large number of microorganisms from soils and in the course of investigations and studies directed to the discovery of antitumor compounds from the products, found out that an actinomycete belonging to the genus Streptomyces and isolated from a soil sample collected in Ichikawa-shi, Chiba-ken, Japan, produced novel HP530 compounds having excellent antitumor activity in the culture medium. The inventors succeeded in forming derivatives of this HP530 compounds by deacetylating or acylating them and completed the present invention by clarifying their physicochemical and biological properties.

Namely, the present invention provides novel HP530 compounds and their derivatives expressed by the following structural formula or their pharmaceutically permissible salts:

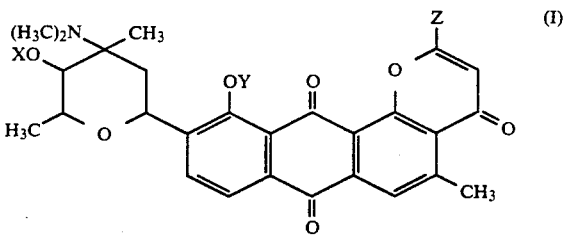

where X is an acyl group of 2 to 4 carbon atoms or hydrogen atom, Y is an acyl group of 2 to 4 carbon atoms or hydrogen atom and Z is a group expressed by the following formula (II), (III) or (IV):

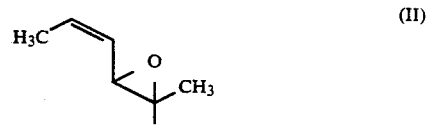

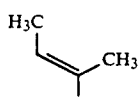

(IV)

The present invention provides also processes for the preparation of HP530 compounds and their pharmaceutically permissible salts characterized by cultivating HP530 producing microorganism belonging to the genus Streptomyces and collecting the HP530 compounds expressed by the structural formula described above from the culture broth and processes for the preparation of derivatives of HP530 compounds and their pharmaceutically permissible salts by deacetylating or acylating the HP530 compounds.

Examples of the $C_2$-$C_4$ acyl group in the definition of the general formula (I) described above include an acetyl group, a propionyl group, a butyryl group and an isobutyryl group.

In the present invention, the compound of HP530 compounds expressed by the general formula(VI) below will be referred to as the "HP530D":

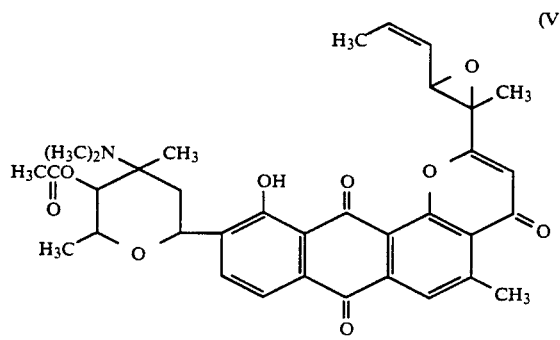

(VI)

Similarly, the compounds expressed by the general formulas (VII) and (VIII) below will be referred to as the "HP530E" and the "HP530G", respectively:

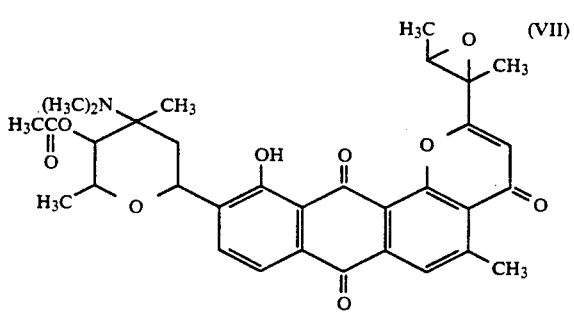

(VII)

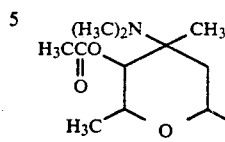

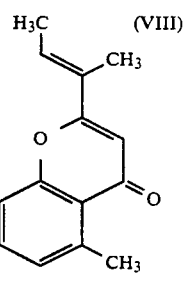

(VIII)

The derivative of HP530 compounds of the general formula (X) obtained by deacetylating HP530D described above will be referred to as the "deacetyl HP530D" and the derivative of the formula (XI)obtained by deacetylating the HP530E will be referred to as the "deacetyl HP530E", respectively:

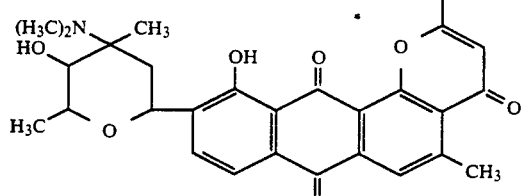

(X)

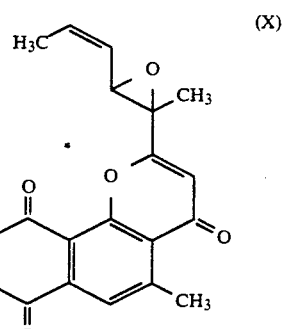

(XI)

The term "deacetylation" used hereby embraces deacetylation of HP530D or HP530E by stirring in methanol or by treating with a base in a solvent.

The Streptomyces sp. HP530 strain producing the HP530 compounds of the present invention has the following taxonomical properties.

(1) Morphological characteristics

Substrate mycelium grows abundantly on various media with no fragmentation. An aerial mycelium formed from branched substrate mycelium is yellow to white series and a chain of 10–50 spores is observed in straight to flexuous. The spore had a smooth surface and is cylindrical in shape with a size $0.6 \times 1.2$ μm. No sclerotium, sporangium and zoospore are observed.

(2) Cultural characteristics:

The cultural characteristics on various media are shown in Table 1.

TABLE 1

| Medium | Growth | Aerial mycelium Formation | Aerial mycelium Color | Color of reverse | Soluble pigment |
|---|---|---|---|---|---|
| Yeast extract-malt extract agar (ISP2) | Good | Abundant | pale yellow (89) | deep orange yellow (69) | None |
| Oatmeal agar (ISP3) | Good | Abundant | yellowish white (92) | deep grayish yellow (91) | None |
| Inorganic salt-starch agar (ISP4) | Good | Abundant | yellowish white (92) | strong yellow (84) | None |
| Glycerin-asparagine agar (ISP5) | Moderate | Abundant | yellowish white (92) | vivid deep redish purple (243) | None |
| Peptone-yeast extract agar (ISP6) | Good | Abundant | pale orange yellow (73) | None | brownish orange |
| Tyrosine agar (ISP7) | Moderate | Abundant | yellowish white (92) | vivid deep redish purple (243) | None |
| Peptone-nitrate agar (ISP8) | Moderate | Abundant | yellowish white (92) | vivid deep purplish red (257) | None |
| Nutrient agar | Good | Abundant | yellowish white (92) | deep brown (56) | None |
| Czapek's agar | Moderate | Moderate | pale greenish yellow (104) | vivid deep purplish red (257) | None |

NOTE: The color index in the parenthesis () is in accordance with ISCC-NBS Color-Name Chart and represents the result observation on the second week at 28° C. on each medium.

(3) Physiological characteristics:

1) Growth temperature range (yeast-malt extract agar, incubation for 14 days): 15°–37° C.
2) Growth pH range (yeast-malt extract agar, 28° C., incubation for 14 days): pH 5.5–11.4
3) Gelatin liquefaction: positive
4) Hydrolysis of starch: positive
5) Coagulation of skim milk: positive
6) Peptonization of skim milk: positive
7) Reduction of nitrate: positive
8) Decomposition of cellulose: negative
9) Utilization of carbon sources (Pridham-Gottlieb agar, 28° C., incubation for 14 days):
   positive utilization: L-arabinose, D-xylose, L-rhamnose, D-glucose, D-galactose, D-fructose, D-mannitol, salicin
   negative utilization sucrose, raffinose, inositol (4) Cell wall type As a result of analysis of diaminopimelic acid of the whole cell, it is found to be of LL type.

The taxonomical properties of the HP530 strain described above can be summarized as follows. It contains LL-diaminopimelic acid and the aerial mycelia is straight to flexuous with smooth spore surface. The aerial mycelia is yellow series while the substrate mycelium is yellow to purple. Brown to orange soluble pigments are produced in the peptone-yeast agar.

These properties indicate that the HP530 strain is the one that belongs to the genus Streptomyces and closely resembles *Streptomyces fluorescens* and *Streptomyces puniceus* from "Bergey's Manual of Determinative Bacteriology", 8th Edition and the "International Journal of Systematic Bacteriology", Vol. 18, pp. 69, 279 (1968), Vol. 19, pp. 391 (1969) and Vol. 22, pp. 265 (1972) of the ISP report.

However, the *Streptomyces fluorescens* differs from this strain in the color of the substrate mycelium and the *Streptomyces puniceus* differs from this strain in that the former does not utilize L-arabinose but produces a blue soluble pigment.

The above made us to presume that this strain is a strain belonging to the genus Streptomyces and it has been deposited in the F.R. I., Agency of Industrial Science and Technology, Japan, as FERM BP-2786 in the name of the Streptomyces sp. HP530.

The HP530 compounds in accordance with the present invention can be produced by inoculating the HP530 strain described above in a medium containing those nutrient sources which the microorganism can utilize generally and incubating the strain under an aerobic condition. Since the properties of the HP530 strain are likely to change easily as observed in many other actinomycetes, all of natural mutants of the HP530 strain, its artificial mutants (by U.V. irradiation, cobalt 60 irradiation, addition of chemical mutagenic agents, etc) and its transformed strain and gene recombination strain can be used as the HP530 compounds producing strains so long as they have the capacity for producing the HP530 compounds besides the HP530 strain described above.

Synthetic, semi-synthetic and natural media that are used generally for the cultivation of the actinomycetes can be used as the nutrient medium. Examples of carbon sources include glucose, fructose, glycerin, starch, dextrin, molasses, vegetable and animal oils and furthermore, hydrocarbons and alcohols either alone or in combination. Natural or organic or inorganic nitrogen compounds such as soybean powder, peptone, wheat emryo bud, meat extract, malt extract, cotton seed oil, corn steep liquor, oatmeal, Pharmamedia (registered trade name), ammonium sulfate, ammonium chloride, sodium nitrate, ammonium nitrate, urea, sodium glutaminate, and the like, can be used either alone or in combination as the nitrogen sources. It is effective to use, whenever necessary, either alone or in combination those inorganic salts such as calcium carbonate, sodium chloride, copper sulfate, manganese chloride, zinc chloride, etc which can generate such ions as sodium, potassium, calcium, magnesium, cobalt, chlorine, phosphoric acid, sulfuric acid, and other ions. Such antifoaming agents as Silicone KM73 (registered trade name), Adecanol (registered trade name), and the like, also can be added appropriately.

Cultivation methods that are generally used for the production of biologically active substances such as antibiotics can be employed as the cultivation method in the present invention. Preferred is an aerobic culture method and particularly, the most suitable method is a submerged aerobic culture method. The incubation temperature is from 25° C. to 37° C. but preferably, the incubation is conducted generally at 30° C. Producibility of the HP530 compounds varies with the medium or incubation condition employed but generally, its accumulation reaches the maximum within three to six days. When accumulation reaches the maximum, the incubation is terminated and the active principles are recovered from the culture broth and purified.

Recovery and purification of the HP530 compounds from the culture in the present invention can be carried out in view of the fact that these compounds are lipophilic as will be illustrated in the later Examples. In other words, the culture broth is separated into the culture filtrate and the cake containing the mycelial cake by filtration or centrifugal separation. The compounds of the invention is extracted with various solvents (acetone, chloroform, ethyl acetate, etc) in a single use or combination HP530 compounds transferred to the solvent can be isolated and purified by various following methods In other words, the isolation/purification procedures are carried out by use of supports such as synthetic resins (Diaion HP-20, a product of Mitsubishi Kasei K.K.; Amberlite XAD-2, a product of Rohm & Haas Co.), gel filtration agents (Sephadex LH-20, a product of Pharmacia Co.; Toyopearl HW-40, a product of Toso Co.), silica gel, cellulose, alumina, chemically modified silica gel, and the like, either alone or in suitable combinations.

The process for the preparation of deacetyl HP530D and deacetyl HP530E (which are the derivatives of HP530 compounds of the invention) obtained by deacetylating them dissolving the aforementioned HP530D or HP530E compound under solution at $-18°$ C. to reflux of the solvent, preferably at room temperature with agitation, forming thereby deacetyl HP530D or deacetyl HP530E in the reaction solution Alternatively, when HP530D or HP530E is dissolved in a solvent and is treated, whenever necessary, with an ordinary base, deacetyl HP530D or deacetyl HP530E is formed in the reaction solution Examples of the solvents used for the process described above include methanol, ethanol, chloroform, dichloromethane, benzene, toluene, xylene, acetonitrile, dioxane, tetrahydrofuran, and the like. Among them methanol is used preferably. Examples of the bases used for the process described above include potassium hydroxide, sodium hydroxide, calcium carbonate, pyridine, triethylamine, sodium methoxide, sodium ethoxide, and the like Recovery and purification of deacetyl HP530D and deacetyl HP530E from the reaction solution in the present invention can be carried out by utilizing lipophilic properties of these compounds, as will be demonstrated in the later Examples. In other words, deacetyl HP530D and deacetyl HP530E extracted with various solvents (chloroform, ethyl acetate, etc) can be purified by the following various methods. The purification procedures are carried out using supports such as synthetic resins (Diaion HP-20, a product of Mitsubishi Kasei K.K.; Amberlite XAD-2, a product of Rohm & Haas Co.), gel filtration agents (Sephadex LH-20, a product of Pharmacia Co., Toyopearl HW-40, a product of Toso Co.) silica gel, cellulose, alumina, chemically modified silica gel, etc, either alone or in suitable combinations.

The acylated derivatives of the HP530 compounds are produced with some agents; acetic anhydride, acetyl chloride, propionic anhydride, propyonil chloride, butyric anhydride, n-butyryl chloride, isobutyryl chloride and isobutyric anhydride. The temperature requirement is from $-10°$ C. to $100°$ C. A base must be used in this acylation. Sodium acetate produced monoacyl derivatives, and pyridine, dimethylaminopyridine or triethylamine yielded diacyl derivatives.

The physico-chemical properties of the acylated derivatives obtained by the preparation process described above are illustrated in the later Examples, and as a result of further studies, the chemical structures of the HP530 compounds and their derivatives are determined as the structures described already.

Since no compound having the same physico-chemical properties with those described above is known, the HP530 compounds and their derivatives are determined and found to be novel compounds.

Definite examples of the salts of the HP530 compounds and their derivatives of the invention in the form of acid addition salts include inorganic salts such as chlorides, sulfates and phosphates and organic salts such as acetates, lactates, propionates, maleates, oleates, palmitates, citrates, succinates, tartrates, fumarates, glutaminates, pantothenates, laurylsulfonates, and the like.

Biological activities of the HP530 compounds and their derivatives the present invention are illustrated below.

a) Antimicrobial activities

The minimum inhibitory concentrations (MIC's) of the HP530 compounds and their derivatives of the invention against bacteria and fungi are shown in Table 2. The HP530 compounds and their derivatives exhibit unambiguously the antimicrobial activities against the bacteria and fungi.

TABLE 2

| Test organism | MIC (µg/ml) | | | | |
| --- | --- | --- | --- | --- | --- |
| | HP530D | HP530E | HP530G | Deacetyl HP530D | Deacetyl HP530E |
| Bacillus subtilis M45Rec⁻ | 0.4 | 0.2 | 3.2 | 0.4 | 0.2 |
| Bacillus subtilis H17Rec⁺ | 3.2 | 12.5 | 100 | 12.5 | 6.3 |
| Staphylococcus aureus JCM2151 | 1.6 | 6.3 | 50 | 1.6 | 3.2 |
| Staphylococcus epidermidis JCM2414 | 3.2 | >100 | 25 | 6.3 | 6.3 |
| Micrococcus luteus JCM1464 | 1.6 | 0.8 | 12.5 | 1.6 | 0.4 |
| Escherichia coli JCM1649 | >100 | >100 | >100 | >100 | >100 |
| Klebsiella pneumoniae JCM1662 | >100 | >100 | >100 | >100 | >100 |
| Proteus vulgaris JCM1668 | >100 | >100 | >100 | >100 | >100 |
| Xanthomonas maltophilia JCM1975 | 3.2 | >100 | >100 | 50 | 25 |
| Salmonella typhimurium TA1535 | 1.6 | 0.8 | 100 | 3.2 | 0.4 |
| Candida albicans JCM1542 | 100 | >100 | >100 | >100 | >100 |
| Saccharomyces cerevisiae JCM1499 | 6.3 | >100 | >100 | 50 | >100 | b) Antitumor activities

1) $CDF_1$ mice were inoculated intraperitoneally with $1 \times 10^6$ cells of mouse fibrosarcoma Meth-A cell line on day 0. HP530 compounds and their derivatives dissolved in a physiological salt solution were administrated intraperitoneally once a day on day 1-4. Their remedial effect was measured in terms of increase in life span with the result shown in Table 3. Increase in life span is represented by the percentage of the ratio of the mean number of surviving days (T) of the treated groups of mice to the mean number of surviving days (C) of the untreated groups of mice.

TABLE 3

| Dose (mg/kg) | Antitumor Activity T/C (%) | | | | |
|---|---|---|---|---|---|
| | HP530D | HP530E | HP530G | Deacetyl HP530D | Deacetyl HP530E |
| 20.0 | — | >192 | 123 | — | — |
| 10.0 | — | >196 | 115 | — | 83 |
| 5.0 | — | 127 | 123 | — | >187 |
| 2.5 | — | 104 | 112 | — | 183 |
| 2.0 | >215 | — | — | 185 | — |
| 1.25 | — | — | — | — | 107 |
| 1.0 | 192 | — | — | 123 | — |
| 0.5 | 123 | — | — | 108 | — |
| 0.25 | 108 | — | — | 92 | — |

2) Cytotoxicity ($IC_{100}$) against W98 cell line obtained by converting the lung cells of a human emryo by an SV40 virus was examined in the following way. When the HP530 compounds and their derivatives dissolved in methanol were added to culture solutions in such a manner that the culture solutions were prepared final 10% methanol solutions, the cytotoxicity of the HP530 compounds and their derivatives against the growth of the W98 cells in the culture solution was measured as 100% growth inhibiting concentration ($IC_{100}$). The result is shown in Table 4.

As a result, $IC_{100}$ values of the HP530 compounds and their derivatives against the W98 cell showed an extremelly low concentration.

As can be seen clearly from this result and also from Table 3, the HP530 compounds and their derivatives exhibit the antitumor activity.

TABLE 4

| Compound | $IC_{100}$ (μg/ml) |
|---|---|
| HP530D | $6 \times 10^{-4}$ |
| HP530E | $6 \times 10^{-4}$ |
| HP530G | $1.0 \times 10^{-1}$ |
| Deacetyl HP530D | $1.5 \times 10^{-4}$ |
| Deacetyl HP530E | $1.5 \times 10^{-4}$ | c) Acute toxicity

In the acute toxicity tests conducted using three $CDF_1$ mice, HP530D (10 mg/kg), HP530E (20 mg/kg), HP530G (20 mg/kg), deacetyl HP530D (20 mg/kg) and deacetyl HP530E (5 mg/kg) exhibit no toxicity in intraperitonal administration.

In the actual preparation of the HP530 compounds and their derivatives of the present invention, the preparation consists of the compound expressed by their structures and a pharmaceutically permissible excipient. The preparation may be either for peroral administration or for extrabuccal administration.

The peroral dosages include generally the forms of dust, tablet, emulsifiable concentrate, capsule, granule and liquid and definite examples of the excipients for internals include dust. Examples of the excipients for the internal dusts or titurations include milk sugar, starch, dextrin, calcium phosphate, calcium carbonate, synthetic and natural aluminum silicate, magnesium oxide, aluminum hydroxide, magnesium searate, sodium bicarbonate, and the like. Examples of the excipients in the liquid preparation include water, glycerin and single sirup.

The extrabuccal dosage includes the form of injection and ebraces sterile aqueous or water-insoluble liquid preparations, suspenders and emulsifiers. The aqueous solutions and suspenders include, for example, distilled water for injection and physiological salt solution Examples of the water-insoluble liquid preparations and suspenders include propylene glycol, polyethylene glycol, vegetable oils such as olive oil, alcohols such as ethanol, polysorbate 80, and the like. These compositions may further contain adjuvants such as antiseptics, lubricants, emulsifiers, dispersants, and the like. They are sterilized by filtration with bacterial filter, addition of antimicrobial agent or irradiation. They can be used also by preparing in advance a sterile solid composition and then dissolving it in sterile water or a sterile injection solvent just before the time of use.

Each of the preparations described above can be prepared in a customary manner.

When the compounds given such structures are used as a preparation, it is dosed generally in a dose of 0.02-200 mg/day, either perorally or extrabuccally, to an adult.

The above and other novel features of the present invention will become more apparent from the following detailed description when taken in conjunction with the accompanying drawings.

Hereinafter, examples of the present invention will be given. It is to be noted, however, that these examples are merely illustrative but in no way limitative to the present invention.

EXAMPLE 1

A liquid medium consisting of 0.5% of glucose, 3.0% of oatmeal, 1.0% of Pharmamedia (registered trade name), 0.5% of magnesium sulfate, 20 ppm of cobalt chloride and 0.3% of calcium carbonate was adjusted to pH 7.0 and was sterilized at 121° C. for 15 minutes in a 500 ml Erlenmeyr flask into which 100 ml of this medium was charged Streptomyces sp. HP530 (FERM BP-2786) was inoculated from an agar slant medium into this Erlenmeyer flask Shaking culture was carried out at 30° C. for 4 days to prepare a primary seed culture The primary seed culture was then inoculated finally 4% into each of two 3 l Erlenmeyer flasks containing 400 ml of the same medium. Shaking culture was carried out at 30° C. for 4 days to prepare a secondary seed culture and the resulting culture was inoculated finally 30% into each of two 30 l jar fermenter containing the same medium (15 l). And then, the fermentation was carried out with aerating and agitating for 4 days at 30° C., an agitation rate of 250 rpm and an aeration rate of 1 vvm.

The culture was then separated into a cake containing the mycelium and a filtrate by a Sharples centrifugal filter and the resulting cake containing the mycelium was soaked in 5 l of 80% acetone. After agitation at room temperature for 3 hours the solid content such as the mycelium was removed by filtration to obtain an acetone extract solution. Acetone was removed from the extract solution under a reduced pressure and the residue was concentrated 10 times to 500 ml. This concentrate was washed with 1.5 l of n-hexane, and then extracted with 1.5 l of ethyl acetate. The ethyl acetate layer dried over anhydrous sodium sulfate was concentrated under a reduced pressure to give 1.4 g of an oily extract.

The resulting oily extract was dissolved in a small amount of methanol, charged on a column packed with 500 ml of a chemically modified silica gel (YMC ODS- AQ 120-S50, a product of YMC Co.). The column was eluted and washed stepwise with the solvent systems of 0.15% KH$_2$PO$_4$ (pH 3.5)-methanol (1:1), 0.15% KH$_2$PO$_4$ (pH 3.5)-methanol (2:3) and 0.15% KH$_2$PO$_4$ (pH 3.5)-methanol (3:7). Furthermore, chromatography with development and elution by 0.15% KH$_2$PO$_4$ (pH 3.5)-methanol (1:4) was carried out. Fractions exhibiting cytotoxicity against a W98 cell were gathered and concentrated under a reduced pressure to obtain an oily active fraction. The oily active fraction was dissolved in a small amount of chloroform and placed on a preparative thin layer plate (Silica Gel 60, F$_{254s}$, No. 13794, a product of Merck Co.) and chromatography with development by the solvent system of chloroform-methanol (99:1, containing 1% of aqueous ammonia) was carried out. The band containing homogeneous HP530D was collected and eluted with chloroform. The resulting chloroform solution was concentrated under a reduced pressure and then methanol was added to the concentrate, a yellowish red precipitate yielded. This precipitate was collected by filtration, washed with hexane and dried under a reduced pressure to give 17.6 mg of yellowish red powder of pure HP530D. The physico-chemical properties of this compound are tabulated below. Cytotoxicity of this compound against the W98 cell is as described above.

HP530D (a) Molecular weight and molecular formula: 615, $C_{35}H_{37}NO_9$ (b) Mass spectrum (FAB - MS/Pos.): $(M+H)^+ m/z$ 616

(c) High performance liquid chromatography: Elution was conducted by capcell pack C$_{18}$ column (4.6$\phi \times$250, a product of Shiseido K.K.) in a system of 0.15% KH$_2$PO$_4$ (pH 3.5)/methanol =2/8 for a retention time of 7.9 minutes at a flow rate of 1 ml/min.

(d) Ultraviolet absorption spectrum: The spectrum measured in a methanol solution is shown in FIG. 1.

Figure 2:
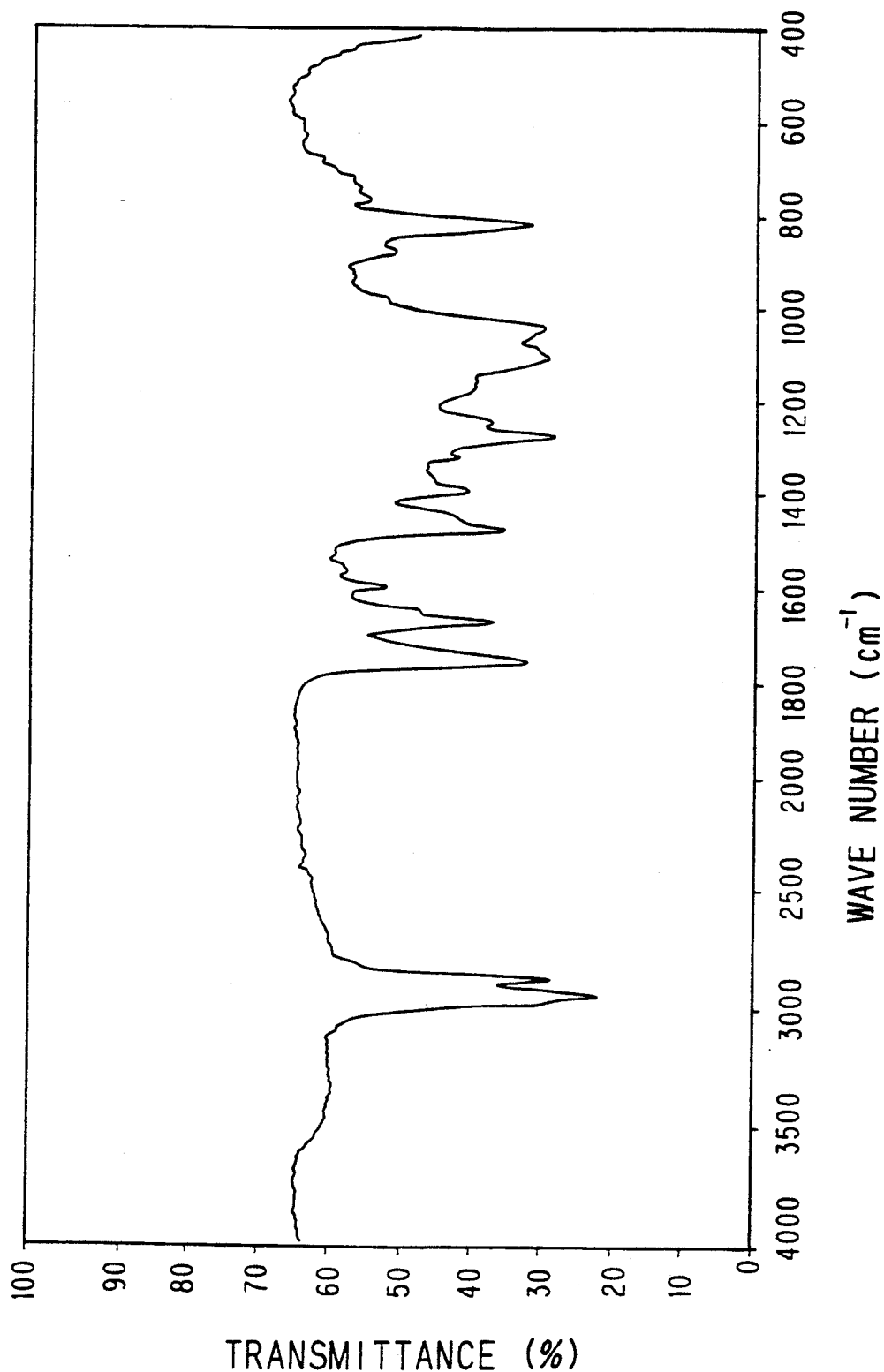
FIG. 2 is an infrared absorption spectrum of HP530D with a potassium bromide tablet.

(e) Infrared absorption spectrum: The spectrum measured using a potassium bromide tablet is shown in FIG. 2.

Figure 3:
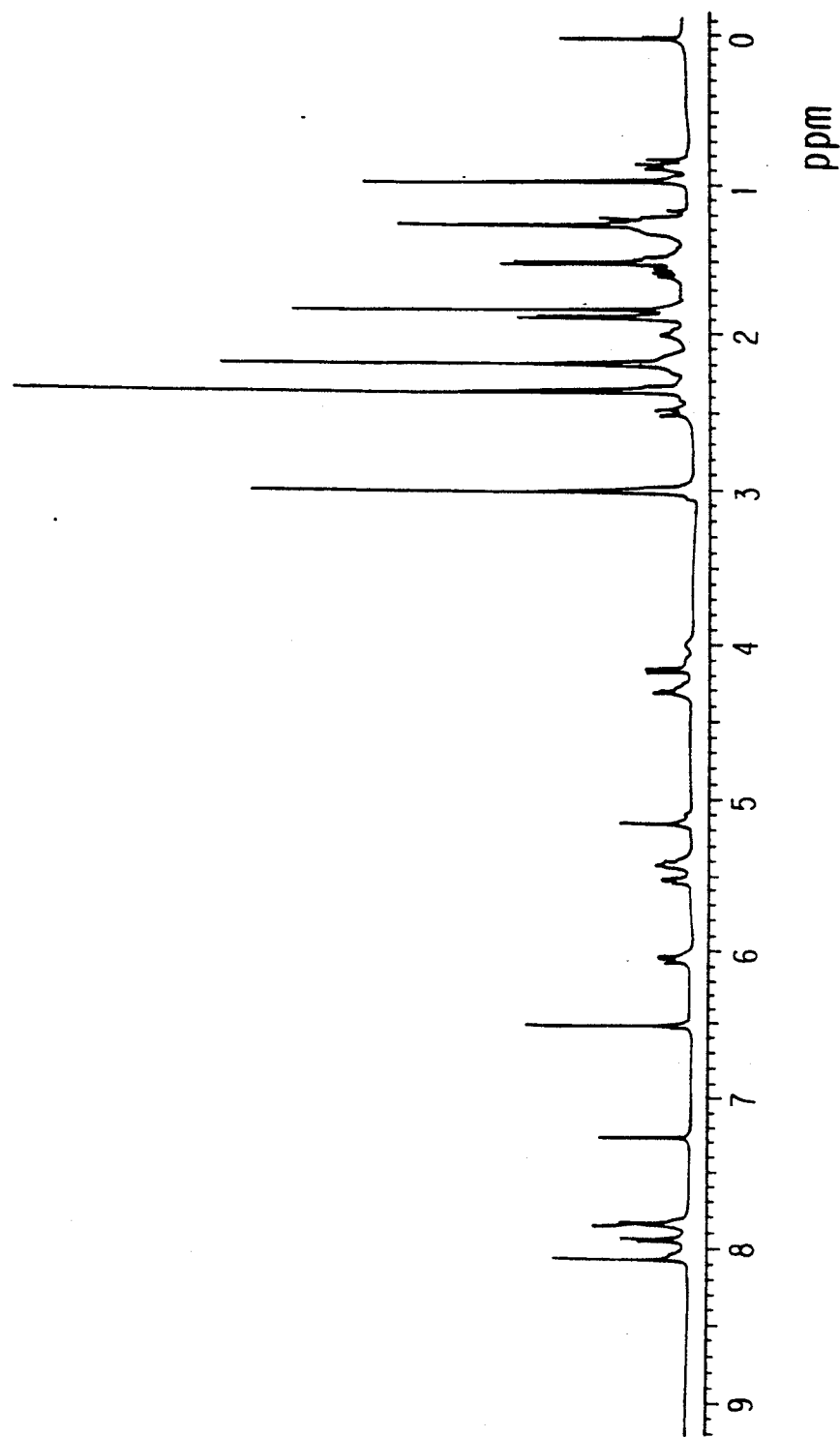
FIG. 3 is a $^1$H-nucleare magnetic resonance spectrum of HP530D in a deutero chloroform solution with tetramethylsilane (TMS) being an internal reference.

(f) $^1$H-nuclear magnetic resonance spectrum The 400 MHz $^1$H-NMR spectrum measured in a deutero chloroform solution is shown in FIG. 3.

(g) $^{13}$C-nuclear magnetic resonance spectrum: The 100 MHz $^{13}$C-NMR spectrum measured in a deutero chloroform solution with TMS being the reference is as follows: δ(ppm): 187.6(s), 181.6(s), 179.0(s), 170.5(s), 167.5 (s), 159.2(s), 156.3(s), 149.8(s), 140.6(s), 136.2(s), 134.0(d), 133.2(d), 130.6(s), 126.5(s), 125.9(d), 123.2(d), 119.9(s), 119.5(d), 115.9(s), 109.8(d), 76.7(d), 70.3(d), 64.1(d), 61.6(d), 59.1(s), 57.7(s), 42.2(t), 39.4(q), 39.4(q), 24.2(q), 21.2(q), 14.7(q), 14.4(q), 13.9(q), 13.9(q)

(h) Solubility: Soluble in acidic water, methanol and chloroform, hardly soluble in ethyl acetate, acetone and n-hexane and insoluble in water (i) Color reactions: Positive to Dragendorff reagent and vanillin sulfate (j) Basic, neutral and acidic distinction: Basic (k) Appearance: Yellowish red amorphous powder

EXAMPLE 2

Thirty liters (30 l) of the culture filtrate obtained in Example 1 was extracted with 30 l of ethyl acetate and the resulting ethyl acetate layer was concentrated under a reduced pressure to give 300 ml of a solution containing HP530D. Thereafter the procedures were carried out in the same manner as in Example 1 and 8.2 mg of yellowish red powder of pure HP530D was obtained.

The physico-chemical properties and cytotoxicity of this compound were the same as those of the compound obtained in Example 1.

EXAMPLE 3

A liquid medium consisting of 0.5% of glucose, 3.0% of oatmeal, 1.0% of Pharmamedia (registered trade name), 0.5% of magnesium sulfate, 20 ppm of cobalt chloride and 0.3% of calcium chloride was adjusted to pH 7.0 and was sterilized at 121° C. for 15 minutes in a 500 ml Erlenmeyer flask containing 100 ml of this medium. Streptomyces sp. HP530 BP-2786) was inoculated from an agar slant into this Erlenmeyer flask. Shaking culture was carried out at 30° C. for 4 days to prepare a primary seed culture. The primary seed culture was then inoculated finally 4% into each of three 3 l Erlenmeyer flasks containing 500 ml of the same medium. Shaking culture was carried out at 30° C. for 4 days to prepare a secondary seed culture and the resulting culture was transferred finally 3% into each of three 30 l jar fermenter containing 15 l of the same medium. And then, the fermentation was carried out with aerating and agitating for 4 days at 30° C., an agitation rate of 250 rpm and an aeration rate of 1 vvm.

The culture broth was separated into a cake containing the mycelium and a filtrate by a Sharples centrifugal filter and the resulting cake containing the mycelium was soaked in 10 l of 80% acetone After agitation at room temperature for three hours, the solid content such as the mycelium was removed by filtration to obtain an acetone extract solution. Acetone was removed from the extract solution under a reduced pressure and the residue was concentrated 10 times to 1,000 ml. This concentrate was washed with 3.0 l of n-hexane, the aqueous layer was extracted with 3.0 l of ethyl acetate. The ethyl acetate layer dried over anhydrous sodium sulfate was concentrated under a reduced pressure to give 7.5 g of an oily extract.

The resulting oily extract was dissolved in a small amount of methanol, charged on a column packed with 1,000 ml of a chemically modified silica gel (YMC ODS-AQ 120-S50, a product of YMC Co.). The column was eluted and washed stepwise with the solvent systems of 0.15% KH$_2$PO$_4$ (pH 3.5)-methanol (1:1), 0.15% KH$_2$PO$_4$ (pH 3.5)-methanol (2:3) and 0.15% KH$_2$PO$_4$ (pH 3.5)-methanol (3:7). Furthermore, chromatography with development and elution by 0.15% KH$_2$PO$_4$ (pH 3.5)-methanol (1:4) was carried out. In this chromatography, HP530E was first eluted and then HP530D. Among them the fractions containing HP530E were gathered, and concentrated under a reduced pressure to obtain an oily active fraction. The oily active fraction was dissolved in a small amount of chloroform and placed on a preparative thin layer plate b(Silica Gel 60, F$_{254s}$, No. 13974, a product of Merck Co.) and chromatography with development by the solvent system of chloroform-methanol (95:5, containing 1% aqueous ammonia) was carried out. The band containing homogeneous HP530E was collected and eluted with chloroform. The resulting chloroform solution was concentrated under a reduced pressure and then methanol was added to the concentrate, a yellow precipitate yielded. This precipitate was collected by filtration, washed with hexane and dried under a reduced pressure to give 7.0 mg of yellow powder of pure HP530E. The physico-chemical properties of this compound are tabulated below. Cytotoxicity of this compound against the W98 cell and its physico-chemical properties are as described already.

HP530E (a) Molecular weight and molecular formula: 589, $C_{33}H_{35}NO_9$ (b) Mass spectrum (FAB - MS/pos.): $(M+H)^+$ m/z 590

(c) High performance liquid chromatography: Elution was conducted by capcell pack $C_{18}$ column (4.6$\phi$×250, a product of Shiseido K.K.) in a system of 0.15% $KH_2PO_4$ (pH 3.5)/methanol =2/8 for a retention time of 5.5 minutes at a flow rate of 1 ml/min.

Figure 4:
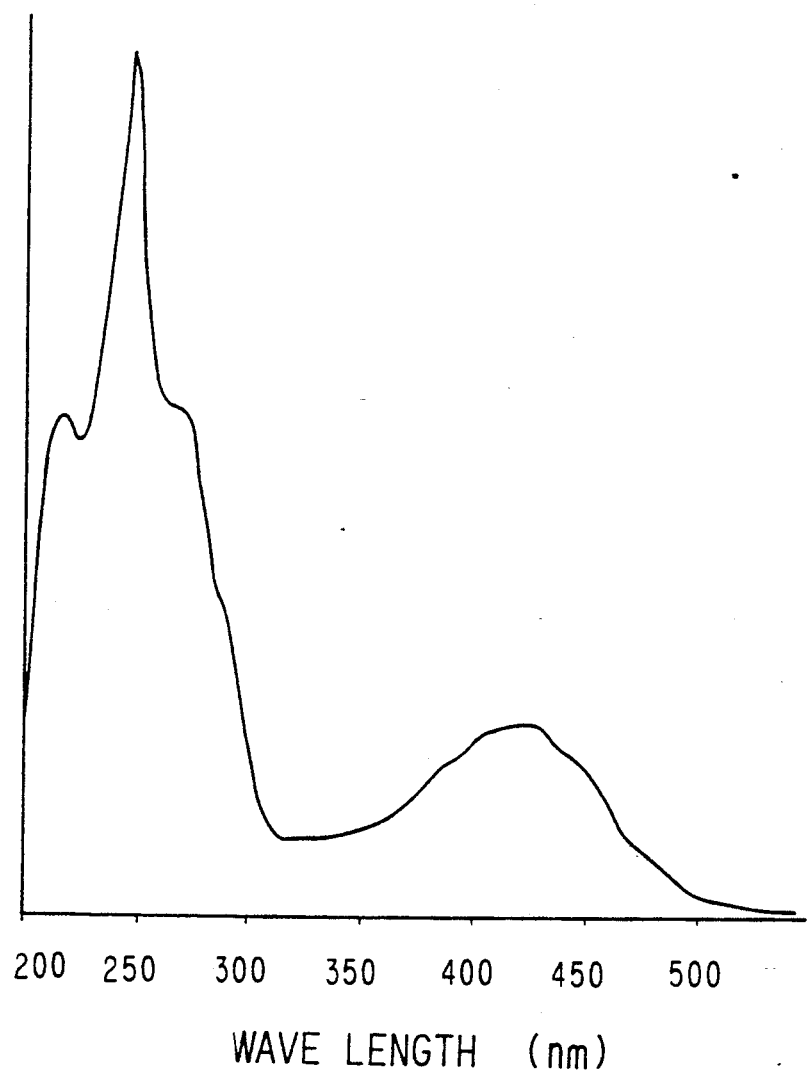
FIG. 4 is a ultraviolet absorption spectrum of HP530E in a methanol solution.

(d) Ultraviolet absorption spectrum The spectrum measured in a methanol solution is shown in FIG. 4.

Figure 5:
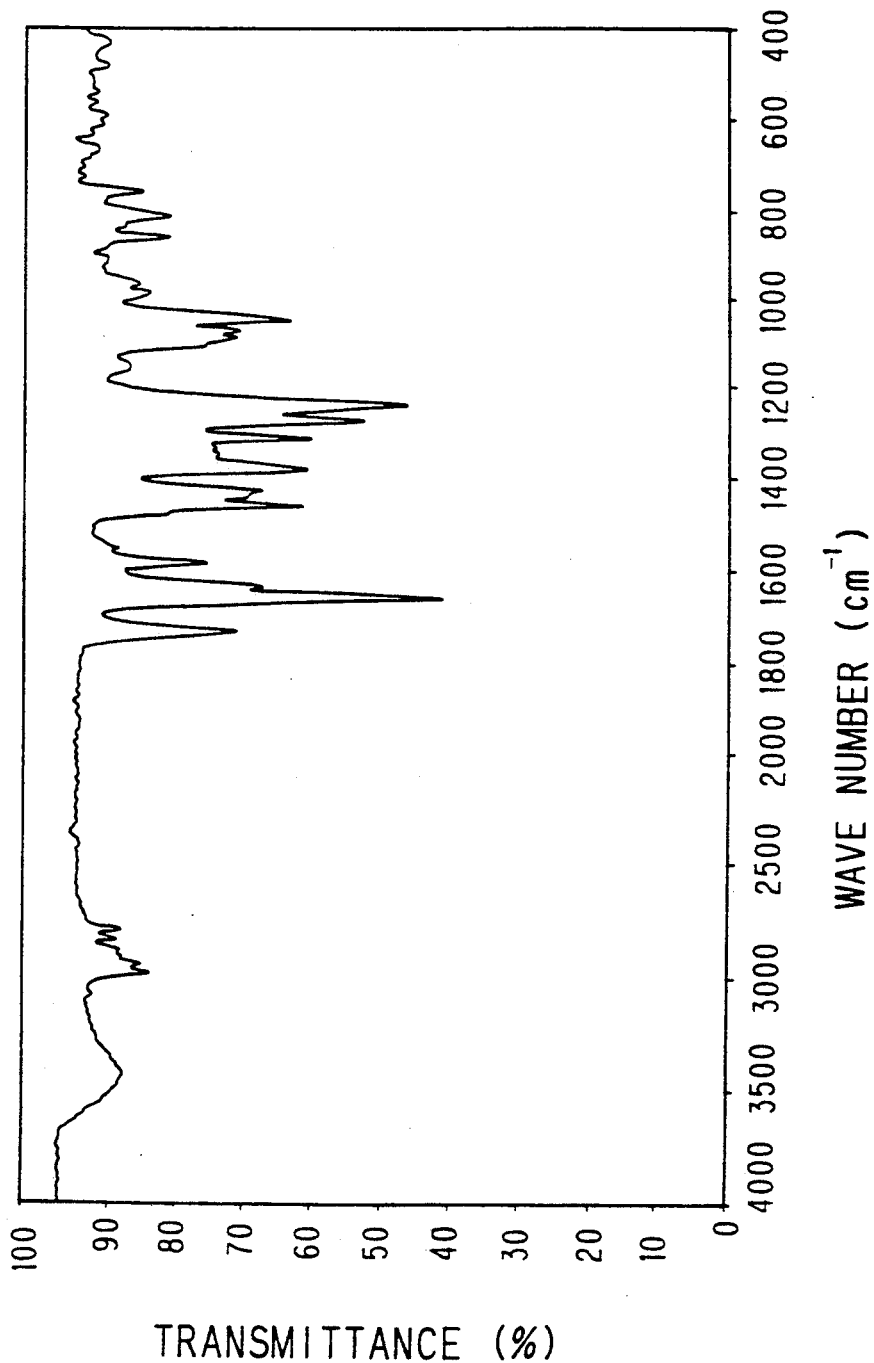
FIG. 5 is an infrared absorption spectrum of HP530E with a potassium bromide tablet.

(e) Infrared absorption spectrum: The spectrum measured using a potassium bromide tablet is shown in FIG. 5.

Figure 6:
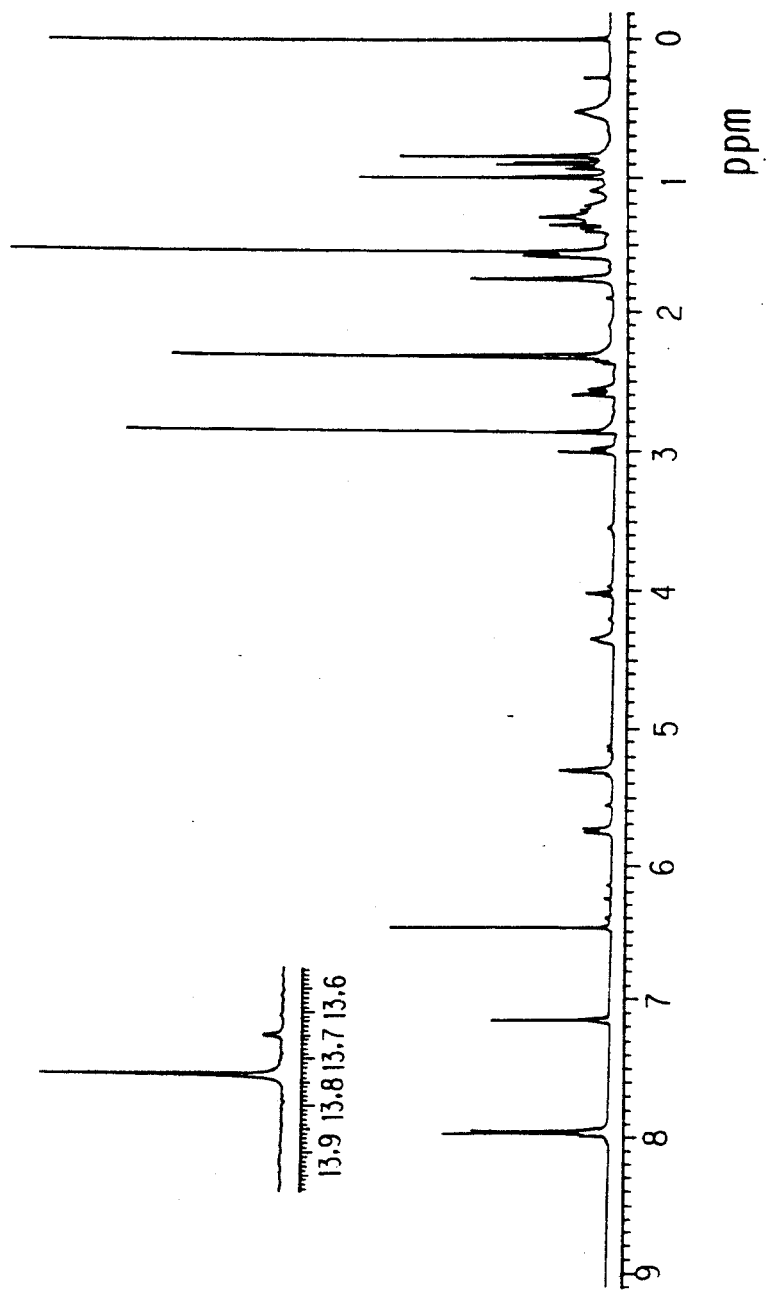
FIG. 6 is a $^1$H-nuclear magnetic resonance spectrum of HP530E in a deutero benzene solution with tetramethylsilane (TMS) being an internal reference.

(f) $^1H$-nuclear magnetic resonance spectrum The 400 MHz $^1H$-NMR spectrum measured in a deutero benzene solution is shown in FIG. 6.

(g) $^{13}C$-nuclear magnetic resonance spectrum The 100 MHz $^{13}C$-NMR spectrum measured in a deutero benzene solution with TMS being the reference is as follows: δ(ppm): 188.1(s), 181.3(s), 178.3(s), 169.6(s), 167.8(s), 159.4(s), 156.3(s), 149.8(s), 140.7(s), 136.2(s), 133.6(d), 131.1(s), 126.7(s), 125.9(d), 119.9(s), 119.4(d), 116.3(s), 109.5(d), 76.9(d), 70.8(d), 64.1(d), 61.7(d), 58.0(s), 57.4(s), 43.0(t), 39.7(q), 39.7(q), 24.0(q), 20.6(q), 14.7(q), 13.8(q), 13.8(q), 13.6(q)

(h) Solubility Soluble in acidic water, methanol, chloroform and benzene, hardly soluble in ethyl acetate, acetone and n-hexane and insoluble in water (i) Color reactions: Positive to Dragendorff reagent and vanillin sulfate (j) Basic, neutral and acidic distinction: Basic (k) Apperance: Yellow amorphous powder

EXAMPLE 4

Forty-five liters (45 0) of the culture filtrate obtained in Example 3 was extracted with 45 l of ethyl acetate and the resulting ethyl acetate layer was concentrated under a reduced pressure to give 450 ml of a solution containing HP530E. Thereafter the procedures was carried out in the same manner as in Example 3 and 2.6 mg of yellow powder of pure HP530E was obtained.

The physicochemical properties and cytotoxicity of this compound were the same as those of the compound obtained in Example 3.

EXAMPLE 5

A liquid medium consisting of 0.5% of glucose, 3.0% of oatmeal, 1.0% of Pharmamedia (registered trade name), 0.5% of magnesium sulfate, 20 ppm of cobalt chloride and 0.3% of calcium carbonate was adjusted to pH 7.0 and was sterilized at 121° C. for 15 minutes in each of three 500 ml Erlenmeyer flasks containing 100 ml of this medium Streptomyces sp. HP530 (FERM BP-2786) was inoculated from an agar slant into each Erlenmeyer flask Shaking culture was carried out at 30° C. for 4 days to prepare a primary seed culture. The primary seed culture was then inoculated finally 4% into each of eleven 3 l Erlenmeyer flasks containing 500 ml of the same medium Shaking culture was carried out at 30° C. for 4 days to prepare a secondary seed culture and the resulting secondary culture was transferred finally 3% into a 300 l jar fermenter containing 180 l of the same medium. And then, the fermentation was carried out with aerating and agitating for 4 days at 30° C., an agitation rate of 250 rpm and an aeration rate of 1 vvm.

The culture was separated into a cake containing the mycelium and a filtrate by a Sharples centrifugal filter and the resulting cake containing the mycelium was soaked in 40 l of 80% acetone. After agitation at room temperature for 3 hours the solid content such as the mycelium was removed by filtration to obtain an acetone extract solution Acetone was removed from the extract solution under a reduced pressure and the residue was concentrated 10 times to 4.0 l. This concentrate was washed with 4.0 l of n-hexane, the residue was extracted with 12.0 l of ethyl acetate. This ethyl acetate layer was dried over anhydrous sodium sulfate and concentrated under a reduced pressure to give 109.8 g of an oily extract.

The resulting oily extract was dissolved in a small amount of methanol, charged on a column packed with 2,000 ml of a chemically modified silica gel (YMC ODS-AQ 120-S50, a product of YMC Co.) and eluted and washed stepwise with the solvent systems of 0.15% $KH_2PO_4$ (pH 3.5)-methanol (1:1), 0.15% $KH_2PO_4$ (pH 3.5)-methanol (2:3) and 0.15% $KH_2PO_4$ (pH 3.5)-methanol (3:7). Furthermore., chromatography with development and elution by 0.15% $KH_2PO_4$ (pH 3.5) methanol (1:4) was carried out. In this chromatography, HP530E, HP530D and HP530G were eluted in order named Among them, fractions containing HP530G were concentrated under a reduced pressure to obtain an oily active fraction. This oily active fraction was dissolved in a small amount of chloroform and placed on a preparative thin layer plate (silica Gel 60, $F_{254s}$, No. 13794, a product of Merck Co.) and then chromatography with development by the solvent system of chloroform-methanol (95:5, containing 1% aqueous ammonia) was carried out. The band containing homogeneous HP530G was collected and eluted with chloroform. The resulting chloroform solution was concentrated under a reduced pressure and then methanol was added to the concentrate, a yellow precipitate yielded The precipitate was collected by filtration, washed with hexane and dried under a reduced pressure to give 8.4 mg of yellow powder of pure HP530G. The physicochemical properties of this compound are tabulated below Cytotoxicity of the compound against the W98 cell is as described above.

HP530G (a) Molecular weight and molecular formula 573, $C_{33}H_{35}NO_8$ (b) Mass spectrum (FAB-MS/Pos.): $(M+H)^+$ m/z 574

(c) High performance liquid chromatography: Elution was conducted by capcell pack $C_{18}$ column (4.6$\phi$×250, a product of Shiseido K.K.) in a system of 0.15% $KH_2PO_4$ (pH 3.5)/methanol =2/8 for a retention time of 10.8 minutes at a flow rate of 1 ml/min.

Figure 7:
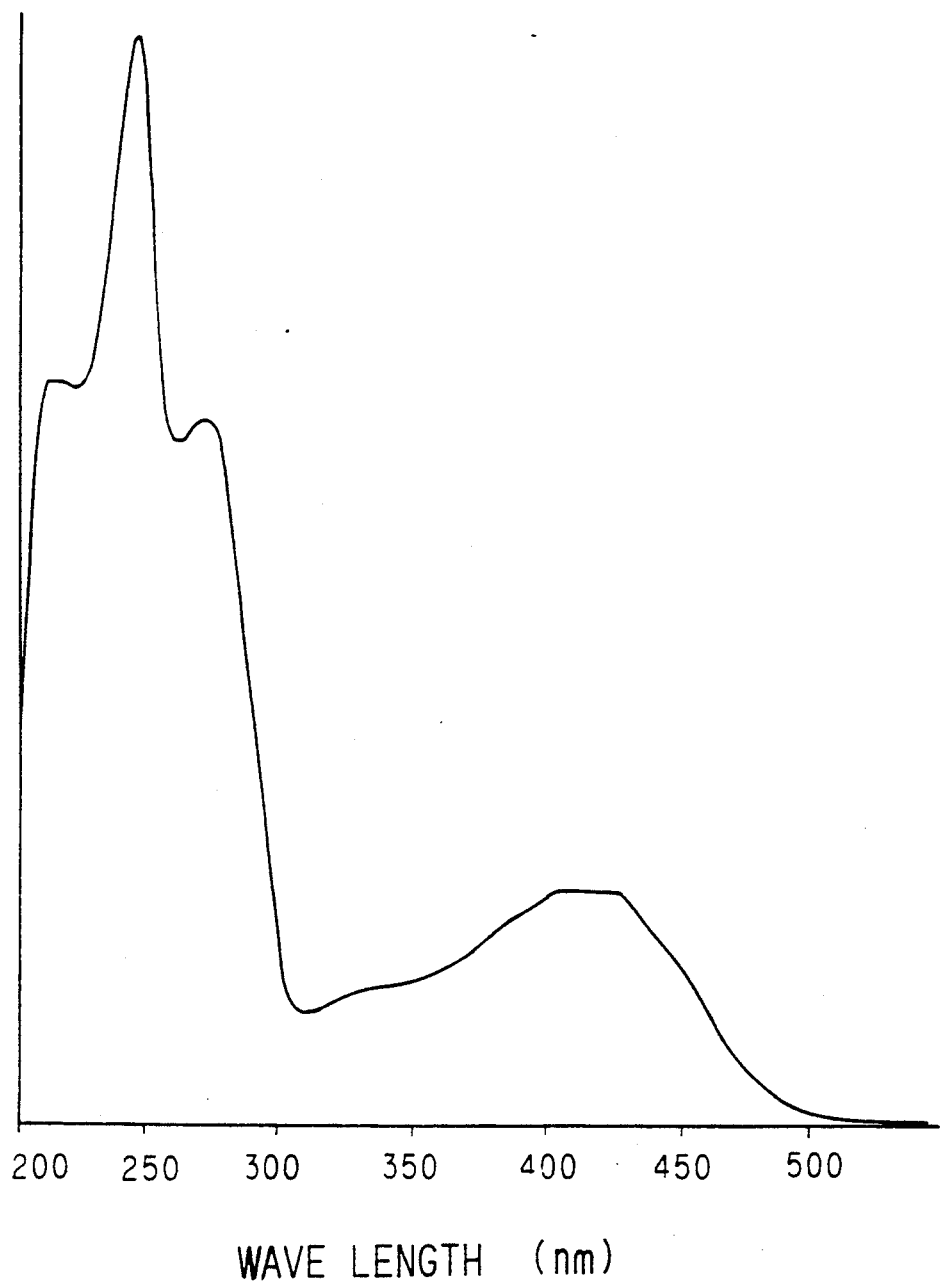
FIG. 7 is a ultraviolet absorption spectrum of HP530G in a methanol solution.

(d) Ultraviolet absorption spectrum: The spectrum measured in a methanol solution is shown in FIG. 7.

Figure 8:
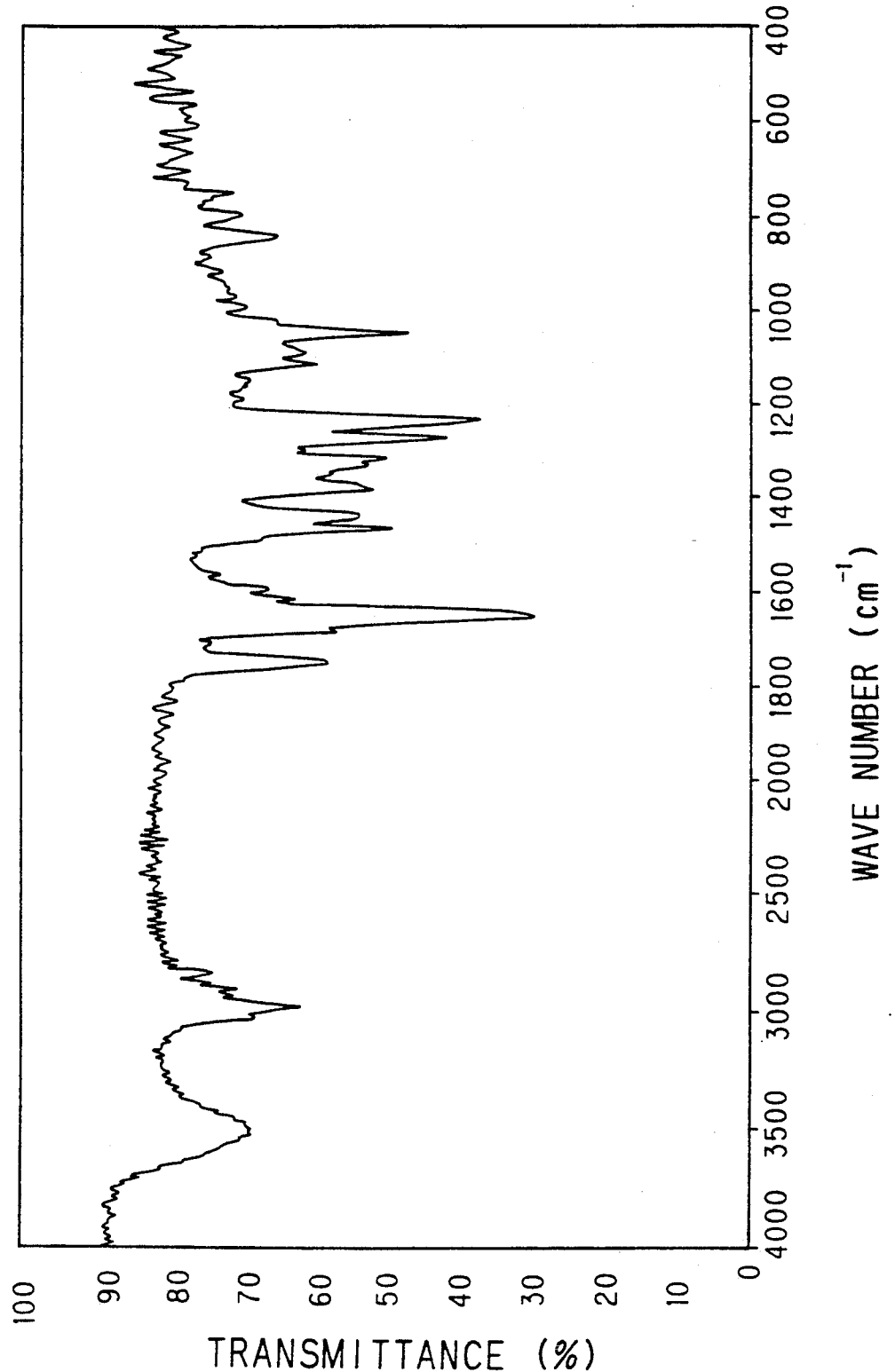
FIG. 8 is an infrared absorption spectrum of HP530G with a potassium bromide tablet.

(e) Infrared absorption spectrum: The spectrum measured using a potassium bromide tablet is shown in FIG. 8.

Figure 9:
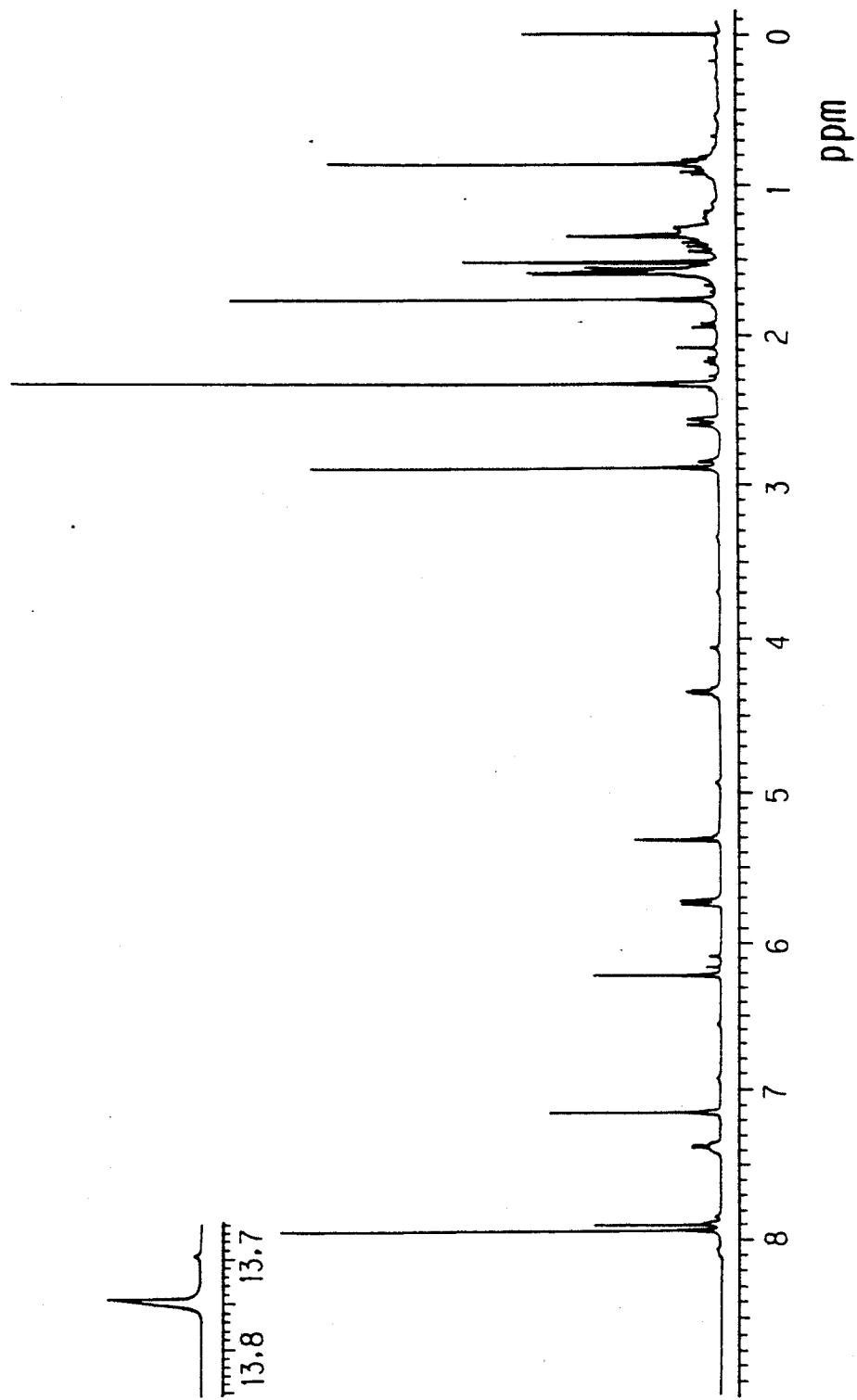
FIG. 9 is a $^1$H-nuclear magnetic resonance spectrum of HP530G in a deutero benzene solution with tetramethylsilane (TMS) being an internal reference.

(f) ¹H-nuclear magnetic resonance spectrum: The 400 MHz ¹H-NMR spectrum measured in a deutero benzene solution is shown in FIG. 9.

(g) ¹³C-nuclear magnetic resonance spectrum: The 100 MHz ¹³C-NMR spectrum measured in a deutero benzene solution with TMS being the reference is as follows. δ(ppm): 188.3(s), 181.2(s), 178.9(s), 169.6(s), 163.4(s), 159.4(s), 156.2(s), 149.7(s), 140.6(s), 136.2(s), 133.5(d), 133.5(d), 131.1(s), 126.6(s), 126.4(s), 125.5(d), 119.7(s), 119.3(d), 116.3(s), 109.0(d), 76.8(d), 70.8(d), 64.2(d), 58.0(s), 42.9(t), 39.7(q), 39.7(q), 24.0(q), 20.7(q), 14.8(q), 14.5(q), 13.8(q), 11.7(q)

(h) Solubility: Soluble in acidic water, methanol, chloroform and benzene, hardly soluble in ethyl acetate, acetone and n-hexane and insoluble in water (i) Color reactions: Positive to Dragendorff reagent and vanillin sulfate (j) Basic, neutral and acidic distinction: Basic (k) Appearance: Yellow amorphous powder

EXAMPLE 6

Hundred-and-eighty liters (180 l) of the culture filtrate obtained in Example 5 was extracted with 60 l of ethyl acetate and the resulting ethyl acetate layer was concentrated under a reduced pressure to give 600 ml of a solution containing HP530G. Thereafter the procedures were carried out in the same manner as in Example 5 and 1.6 mg of yellow powder of pure HP530G was obtained.

The physico-chemical properties and cytotoxicity of this compound were the same as those of the compound obtained in Example 5.

EXAMPLE 7

Fourteen-point-three milligrams (14.3 mg) of HP530D obtained in Examples 1 and 2 was dissolved in 28 ml of methanol and reacted at room temperature for 48 hours Methanol was concentrated under a reduced pressure and the mixture of yellowish red powder of HP530D and deacetyl HP530D was obtained.

Powder of this mixture was dissolved in a small amount of chloroform and placed on a preparative thin layer plate (Silica Gel 60, F$_{254s}$, No. 13794, a product of Merck Co.). Chromatography with development by the solvent system of chloroform-methanol (9:1) was then carried out. The band containing homogeneous deacetyl HP530D was collected and eluted with chloroform-methanol (1:1). The resulting chloroform-methanol was concentrated under a reduced pressure and then methanol was added, a yellowish red precipitate yielded. This precipitate was collected by filtration, washed with hexane and dried under a reduced pressure to give 12.3 mg of yellowish red powder of pure deacetyl HP530D. The physico-chemical properties of this compound are tabulated below. Cytotoxicity of the compound against the W98 cell was as described above.

Deacetyl HP530D (a) Molecular weight and molecular formula: 573, $C_{33}H_{35}NO_8$ (b) Mass spectrum (FAB-MS/Pos.): (M+H)+m/z 574

Figure 10:
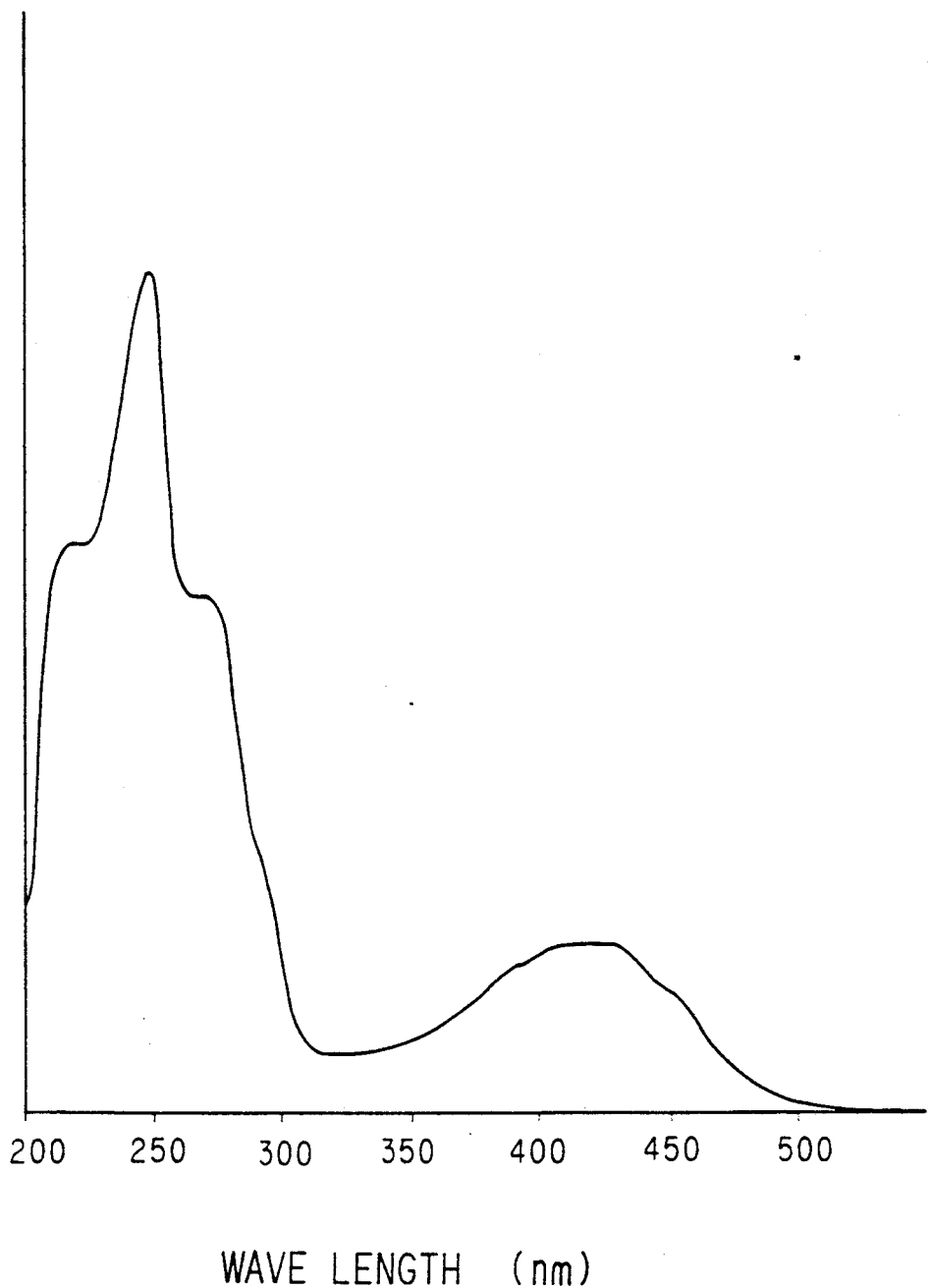
FIG. 10 is a ultraviolet absorption spectrum of deacetyl HP530D in a methanol solution.

(c) High performance liquid chromatography: Elution was conducted by capcell pack $C_{18}$ column (4.6φ×250, a product of Shiseido K.K.) in a system of 0.15% $KH_2PO_4$ (pH 3.5)/methanol =⅓ for a retention time of 6.3 minutes at a flow rate of 1 ml/min (d) Ultraviolet absorption spectrum The spectrum measured in a methanol solution is shown in FIG. 10.

Figure 11:
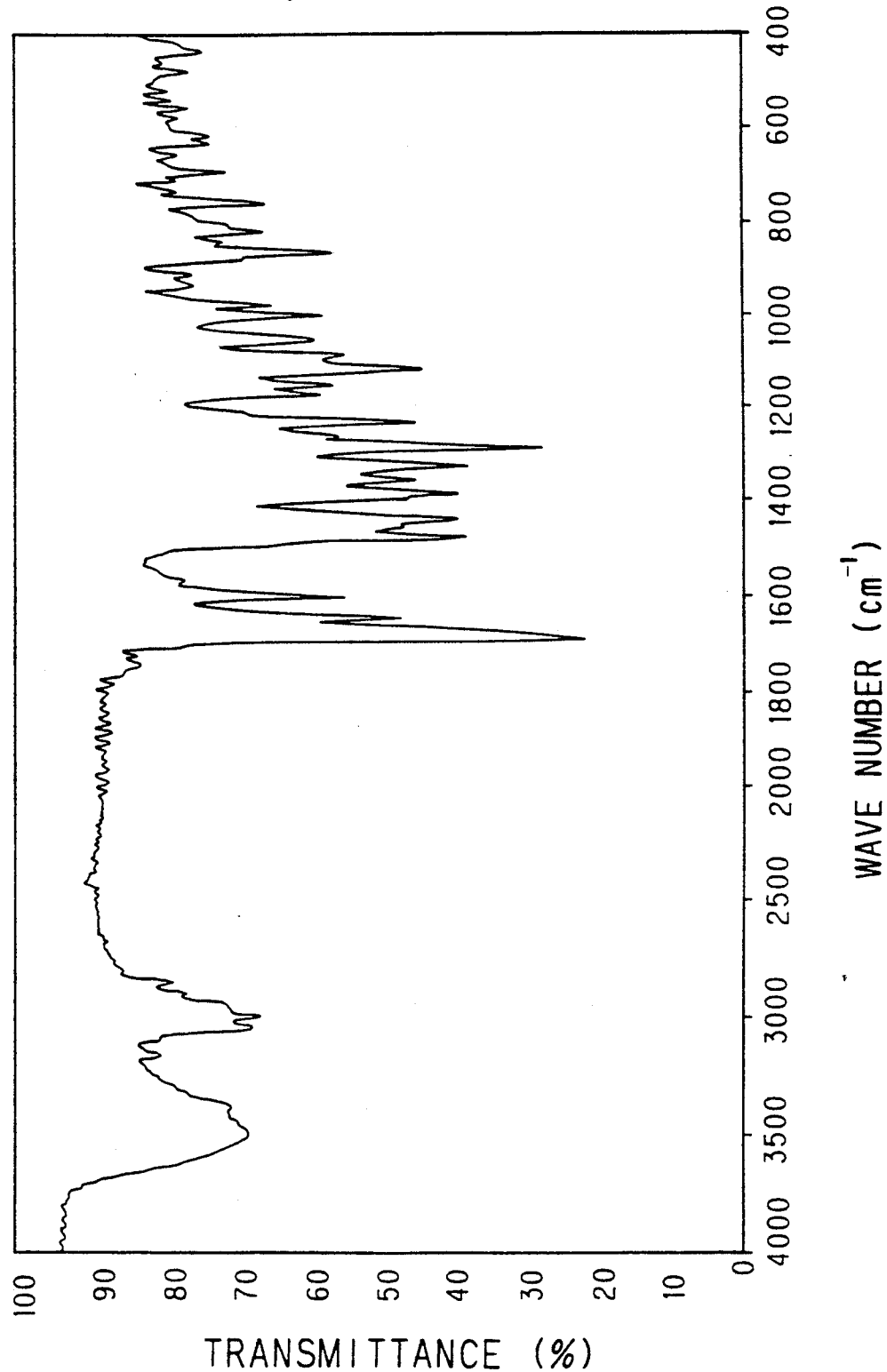
FIG. 11 is an infrared absorption spectrum of deacetyl HP530D with a potassium bromide tablet.

(e) Infrared absorption spectrum The spectrum measured using a potassium bromide tablet is shown in FIG. 11.

Figure 12:
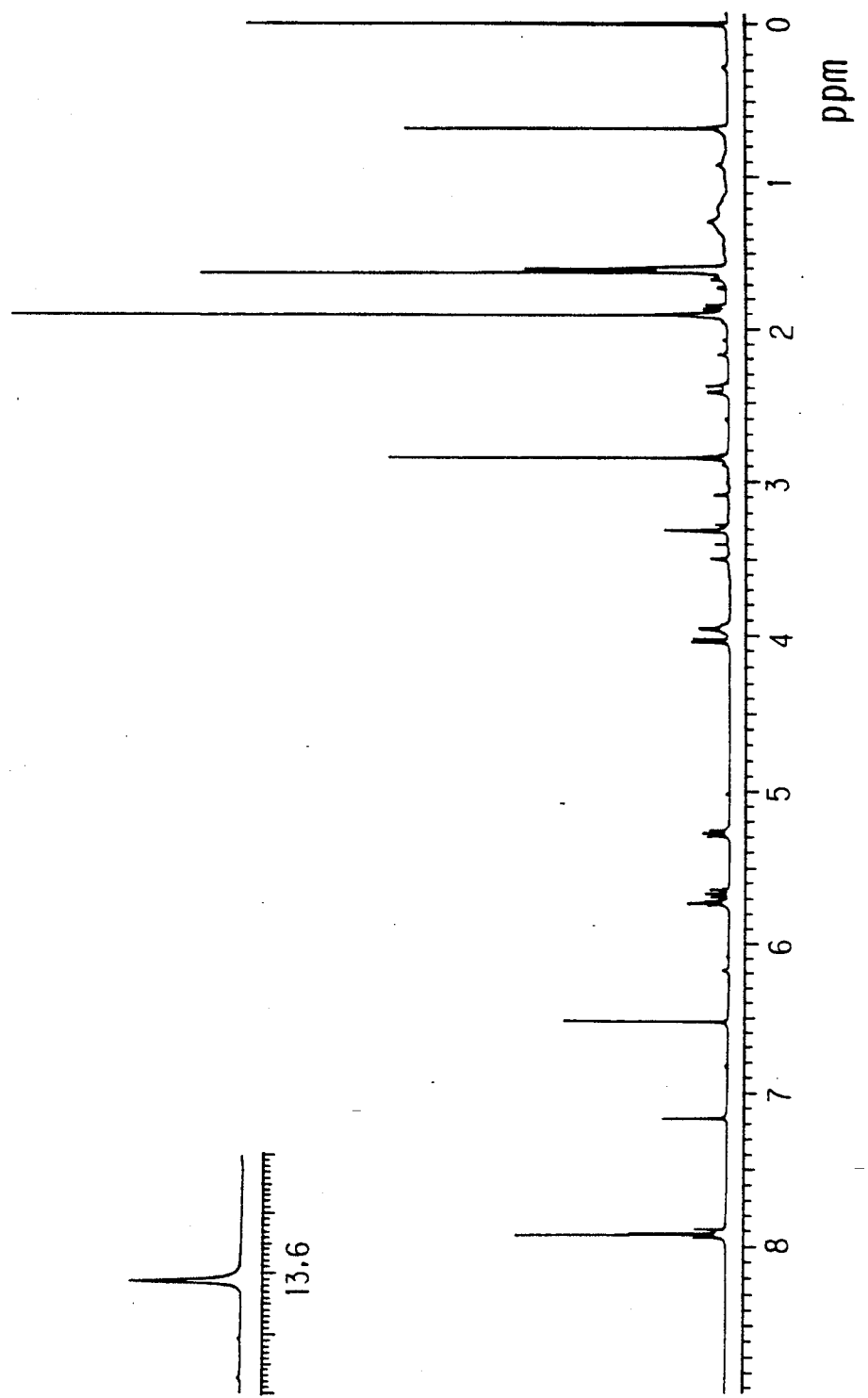
FIG. 12 is a $^1$H-nuclear magnetic resonance spectrum of deacetyl HP530D in a deutero benzene solution with tetramethylsilane (TMS) being an internal reference.

(f) ¹H-nuclear magnetic resonance spectrum The 400 MHz ¹H-NMR spectrum measured in a deutero benzene solution is shown in FIG. 12.

(g) ¹³C-nuclear magnetic resonance spectrum The 100 MHz ¹³C-NMR spectrum measured in a deutero benzene solution with TMS being the reference is as follows. δ(ppm): 187.9(s), 181.3(s), 178.3(s), 167.1(s), 159.7(s), 156.4(s), 149 6(s), 141.5(s), 136.2(s), 133.4(d), 133.3(d), 131.1(s), 126.6(s), 125.7(d), 124.0(d), 119.9(s), 119.2(d), 116.5(s), 109.9(d), 71.2(d), 69.0(d), 67.3(d), 61.5(d), 59.0(s), 58.0(s), 37.1(t), 37.0(q), 37.0(q), 24.0(q), 17.4(q), 14.4(q), 13.7(q), 13.3(q)

(h) Solubility: Soluble in acidic water, methanol, chloroform and benzene, hardly soluble in ethyl acetate, acetone and n-hexane and insoluble in water (i) Color reactions: Positive to Dragendorff reagent and vanillin sulfate (j) Basic, neutral and acidic distinction: Basic (k) Appearance: Yellowish red amorphous powder

EXAMPLE 8

Eight milligrams (8mg) of HP530E obtained in Examples 3 and 4 was dissolved in 16 ml of methanol and reacted at room temperature for 48 hours. Methanol was concentrated under a reduced pressure to obtain the mixture of yellow powder of HP530E and deacetyl HP530E. Powder of this mixture was dissolved in a small amount of chloroform and placed on a preparative thin layer plate (Silica Gel 60, F$_{254s}$, No. 13794, a product of Merck Co.) and chromatography with development by a the system of chloroform-methanol (9:1) was carried out. The band containing homogeneous deacetyl HP530E was collected and eluted with chloroform-methanol (1:1). The resulting chloroform-methanol was concentrated under a reduced pressure and then methanol was added, a yellow precipitate yielded. This precipitate was collected by filtration, washed with hexane and dried under a reduced pressure to give 5.5 mg of yellow powder of deacetyl pure HP530E. The physico-chemical properties of this compound are tabulated below. Cytotoxicity of this compound against the W98 cell was as described above.

Deacetyl HP530E (a) Molecular weight and molecular formula: 547, $C_{31}H_{33}NO_8$ (b) Mass spectrum (FAB-MS/Pos.): (M+H)+m/z 548

(c) High performance liquid chromatography: Elution was conducted by capcell pack $C_{18}$ column (4.6φ×250, a product of Shiseido K.K.) in a system of 0.15% $KH_2PO_4$ (pH 3.5)/methanol =1/3 for a retention time of 6.5 minutes at a flow rate of 1 ml/min.

Figure 13:
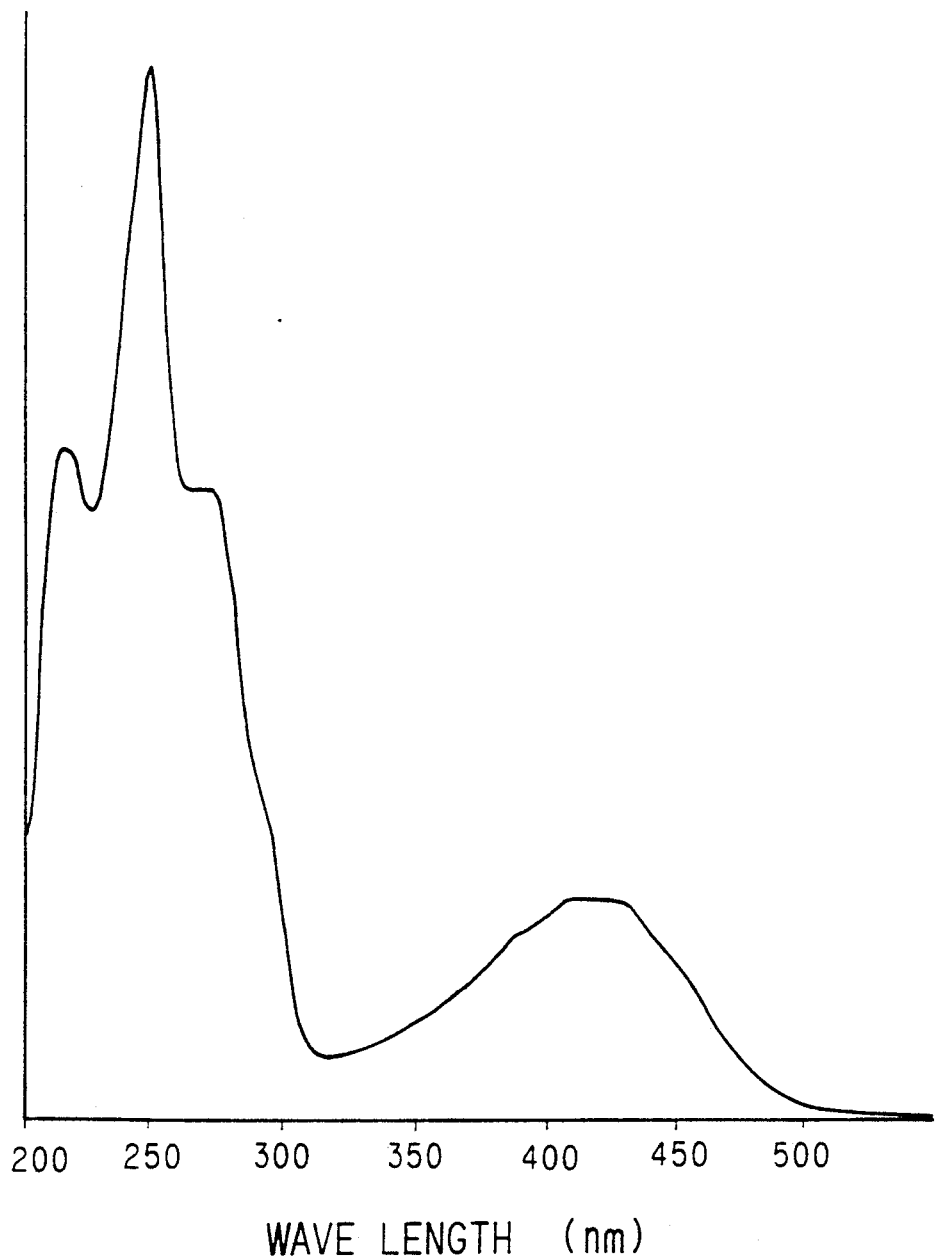
FIG. 13 is a ultraviolet absorption spectrum of deacetyl HP530E in a methanol solution.

(d) Ultraviolet absorption spectrum: The spectrum measured in a methanol solution is shown in FIG. 13.

Figure 14:
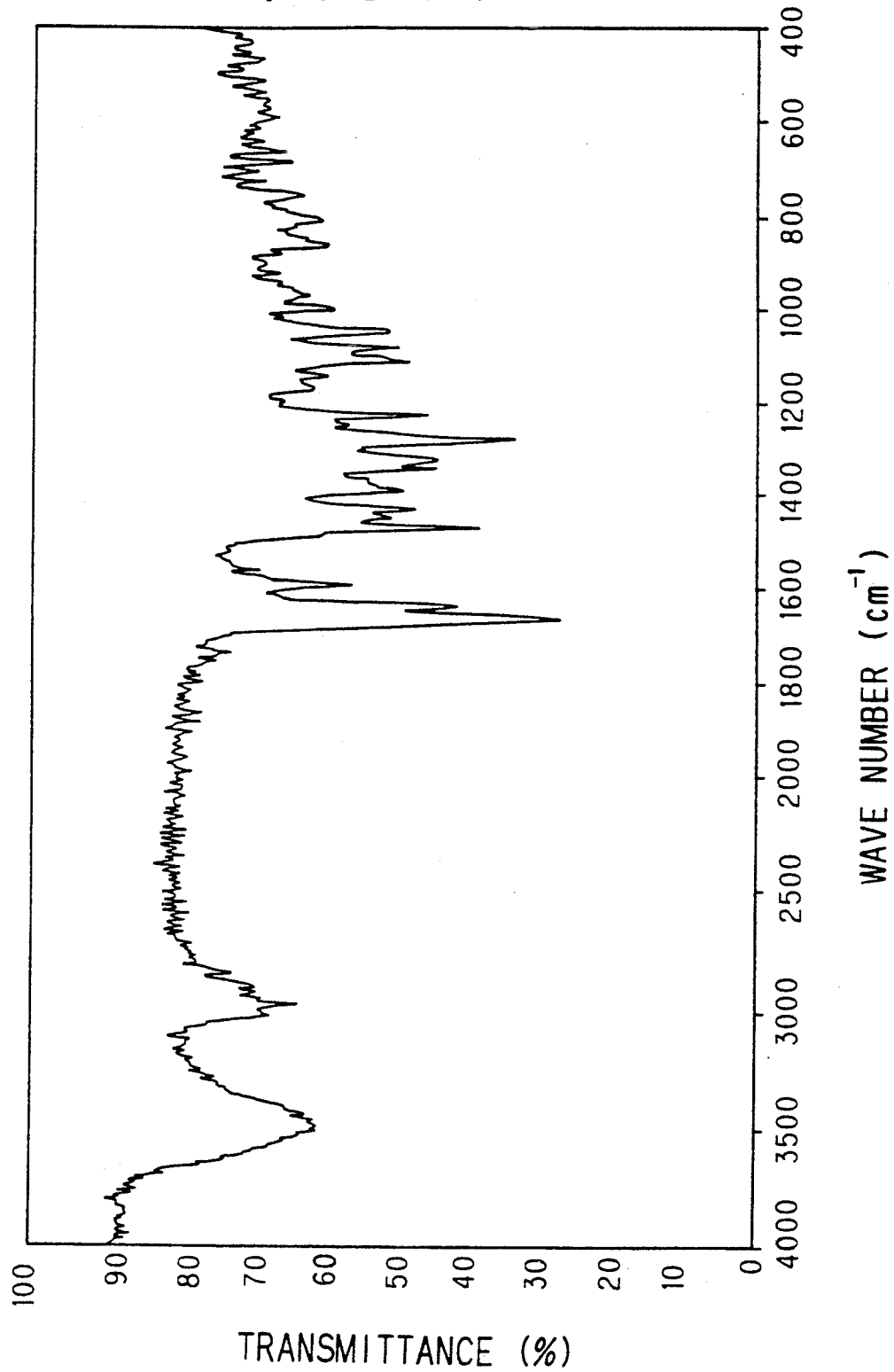
FIG. 14 is an infrared absorption spectrum of deacetyl HP530E with a potassium bromide tablet.

(e) Infrared absorption spectrum The spectrum measured using a potassium bromide tablet is shown in FIG. 14.

Figure 15:
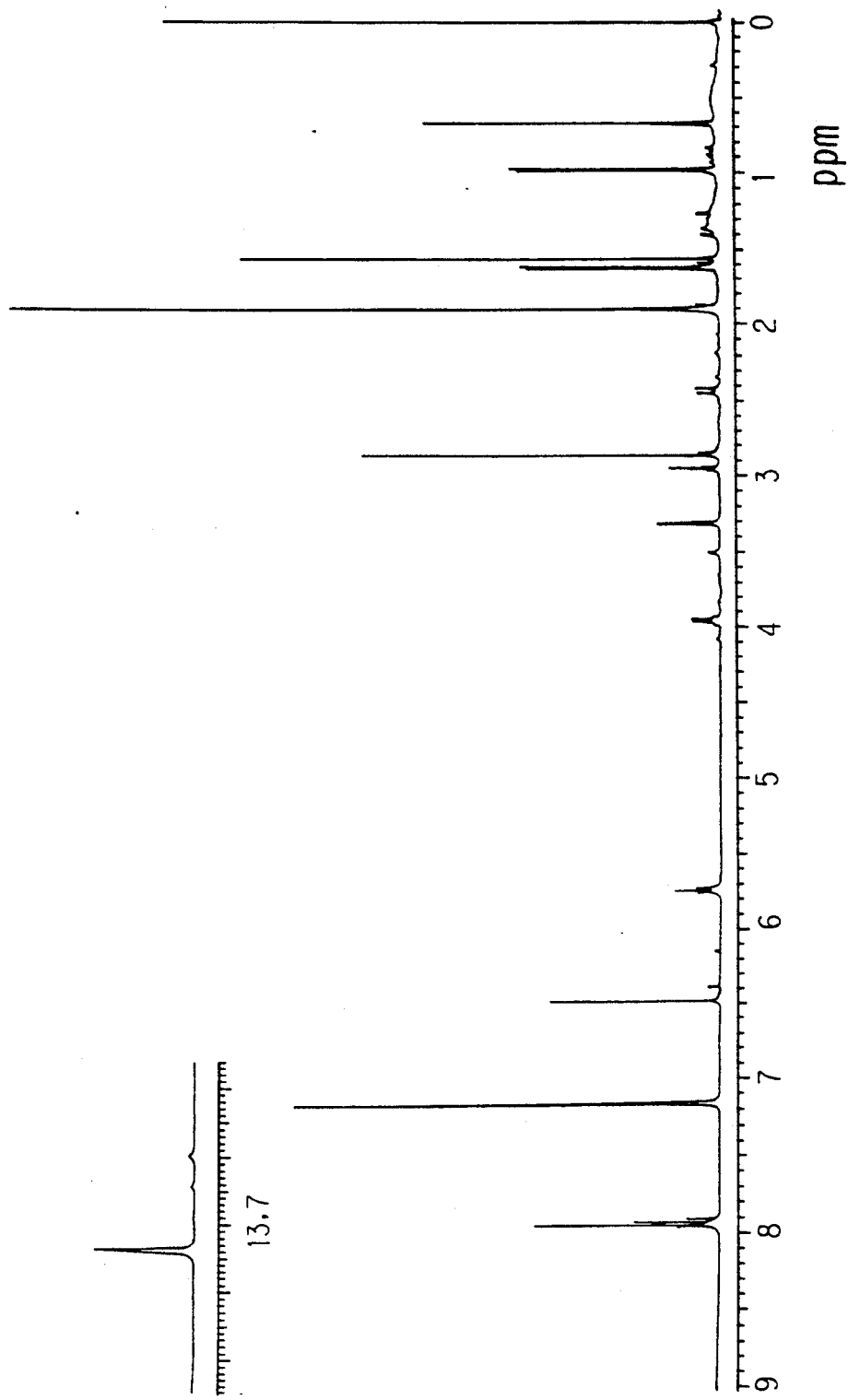
FIG. 15 is a $^1$H-nuclear magnetic resonance spectrum of deacetyl HP530E in a deutero benzene solution with tetramethylsilane (TMS) being an internal reference.

(f) ¹H-nuclear magnetic resonance spectrum The 400 MHz ¹H-NMR spectrum measured in a deutero benzene solution is shown in FIG. 15.

(g) $^{13}$C-nuclear magnetic resonance spectrum The 100 MHz $^{13}$C-NMR spectrum measured in a deutero benzene solution with TMS being the reference is as follows. δ(ppm): 187.9(s), 181.3(s), 178.3(s), 167.9(s), 159.7(s), 156.3(s), 149.7(s), 141.5(s), 136.2(s), 133.3(d), 131.1(s), 126.7(s), 125.8(d), 119.2(s), 119.2(d), 116.5(s), 109.4(d), 71.2(d), 69.0(d), 67.4(d), 61.8(d), 58.0(s), 57.4(s), 37.0(t), 37.0(q), 37.0(q), 24.0(q), 17.4(q), 13.7(q), 13.6(q), 13.3(q)

(h) Solubility: Soluble in acidic water, methanol, chloroform and benzene, hardly soluble in ethyl acetate, acetone and n-hexane and insoluble in water (i) Color reactions: Positive to Dragendorff reagent and vanillin sulfate (j) Basic, neutral and acidic distinction: Basic (k) Appearance: Yellow amorphous powder

EXAMPLE 9

A liquid medium consisting of 0.5% of glucose, 3.0% of oatmeal, 1.0% of Pharmamedia (registered trade name), 0.5% of magnesium sulfate, 20 ppm of cobalt chloride and 0.3% of calcium carbonate was adjusted to pH 7.0 and was sterilized at 121° C. for 15 minutes in a 500 ml Erlenmeyer flask containing 100 ml of this medium. Streptomyces sp. HP530 (FERM BP-2786) was inoculated from an agar slant into this Erlenmeyer flask. Shaking culture was carried out at 30° C. for 4 days to prepare a primary seed culture. The primary seed culture was then inoculated finally 4% into each of three 3 l Erlenmeyer flasks containing 500 ml of the same medium. Shaking culture was carried out at 30° C. for 4 days to prepare a secondary seed culture and the resulting culture was transferred finally 3% into each of three 30 l jar fermenter containing 15 l of the same medium. And then, the fermentation was carried out with aerating and agitating for 4 days at 30° C., an agitation rate of 250 rpm and an aeration rate of 1 vvm.

The culture broth was separated into a cake containing the mycelium and a filtrate by a Sharples centrifugal filter and the resulting cake containing the myselium was soaked in 10 ( of 80% acetone. After agitation at room temperature for 3 hours the solid content such as the mycelium was removed by filtration to obtain an acetone extract solution Acetone was removed from the extract solution under a reduced pressure and the residue was concentrated 10 times to 1000 ml. This concentrate was washed with 3.0 l on n-hexane, and then extracted with 3.0 l of ethyl acetate. The ethyl acetate layer was dried over anhydrous sodium sulfate was concentrated under a reduced pressure to give 7.5 g of an oily extract.

The resulting oily extract was dissolved in a small amount of methanol, charged on a column packed with 1,000 ml of a chemically modified silica gel (YMC ODS-AQ 120-S50, a product of YMC Co.) and eluted and washed stepwise with the solvent systems of 0.15% KH$_2$PO$_4$ (pH 3.5)-methanol (1:1), 0.15% KH$_2$PO$_4$ (pH 3.5)-methanol (2:3) and 0.15% KH$_2$PO$_4$ (pH 3.5)-methanol (3:7). Furthermore, chromatography with development and elution by 0.15% KH$_2$PO$_4$ (pH 3.5)-methanol (1:4) was carried out In this chromatography, HP530E was first eluted, then the mixture of HP530E and HP530H, and HP530D, respectively. Among them, the mixed fractions containing HP530E and HP530H were gathered and concentrated under a reduced pressure to obtain an oily active fraction. The oily active fraction was placed on a preparative thin layer plate (Silica Gel 60, F$_{254s}$, No. 13794, a product of Merck Co.) and chromatography with development by the solvent system of chloroform-methanol (100:1, containing 1% aqueous ammonia) was carried out. The band containing homogeneous HP530H was collected and eluted with chloroform. The resulting chloroform solution was concentrated under a reduced pressure and then methanol was added, a yellow precipitate yielded. This precipitate was collected by filtration, washed with hexane and dried under a reduced pressure to give 3.5 mg of yellow powder of pure HP530H. The physico-chemical properties of this compound are tabulated below.

HP530H (a) Molecular weight and molecular formula: 589, $C_{33}H_{35}NO_9$ (b) Mass spectrum (FAB-MS/Pos.): (m+H)$^+$m/z 590

(c) High performance liquid chromatography Elution was conducted by capcell pack C$_{18}$ column (4.6φ×250, a product of Shiseido K.K.) in a system of 0.15% KH$_2$PO$_4$/methanol=1/3 for a retention time of 7.1 minutes at a flow rate of 1 ml/min.

Figure 16:
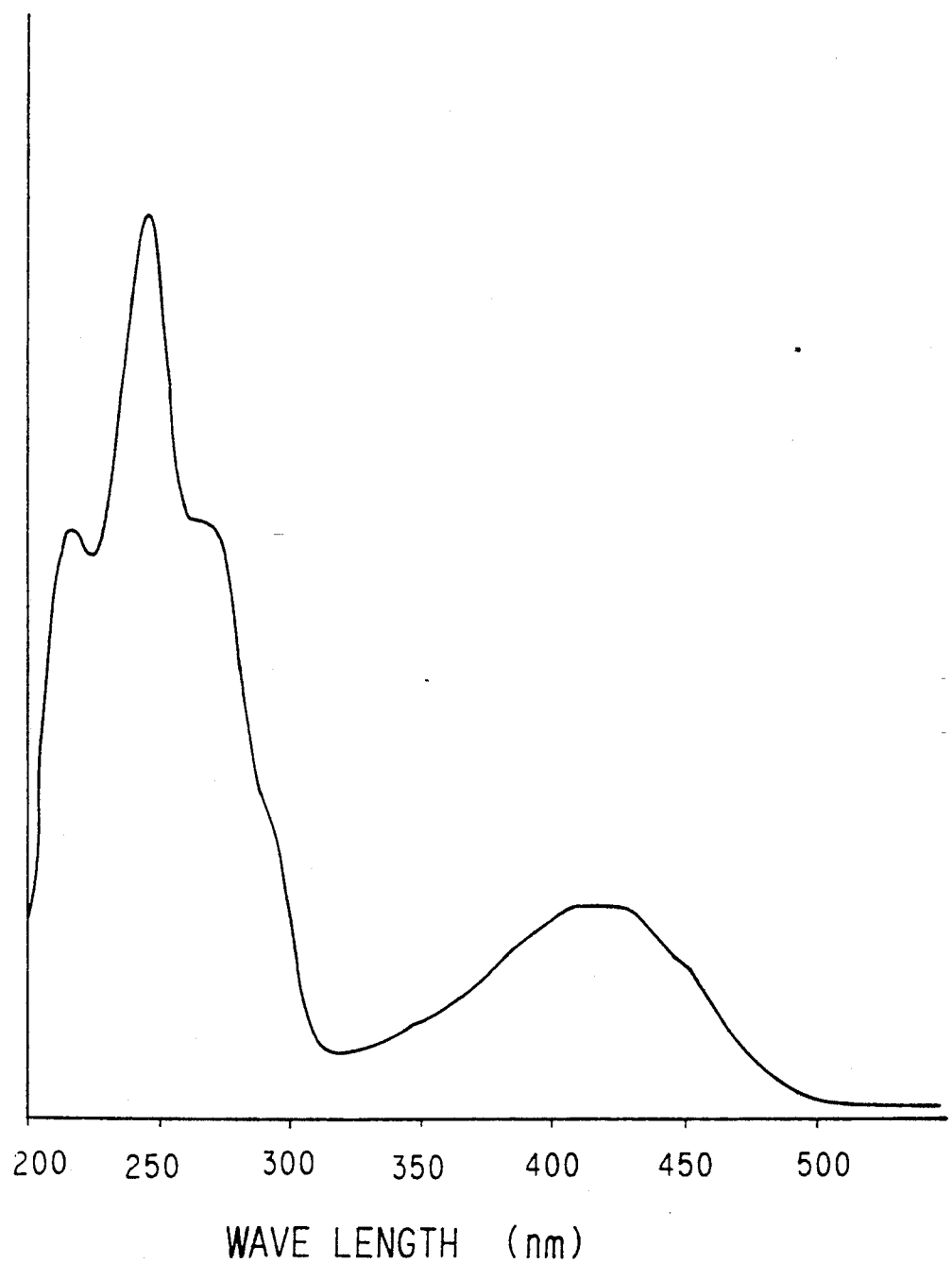
FIG. 16 is a ultraviolet absorption spectrum of HP530H in a methanol solution.

(d) Ultraviolet absorption spectrum The spectrum measured in a methanol solution is shown in FIG. 16.

Figure 17:
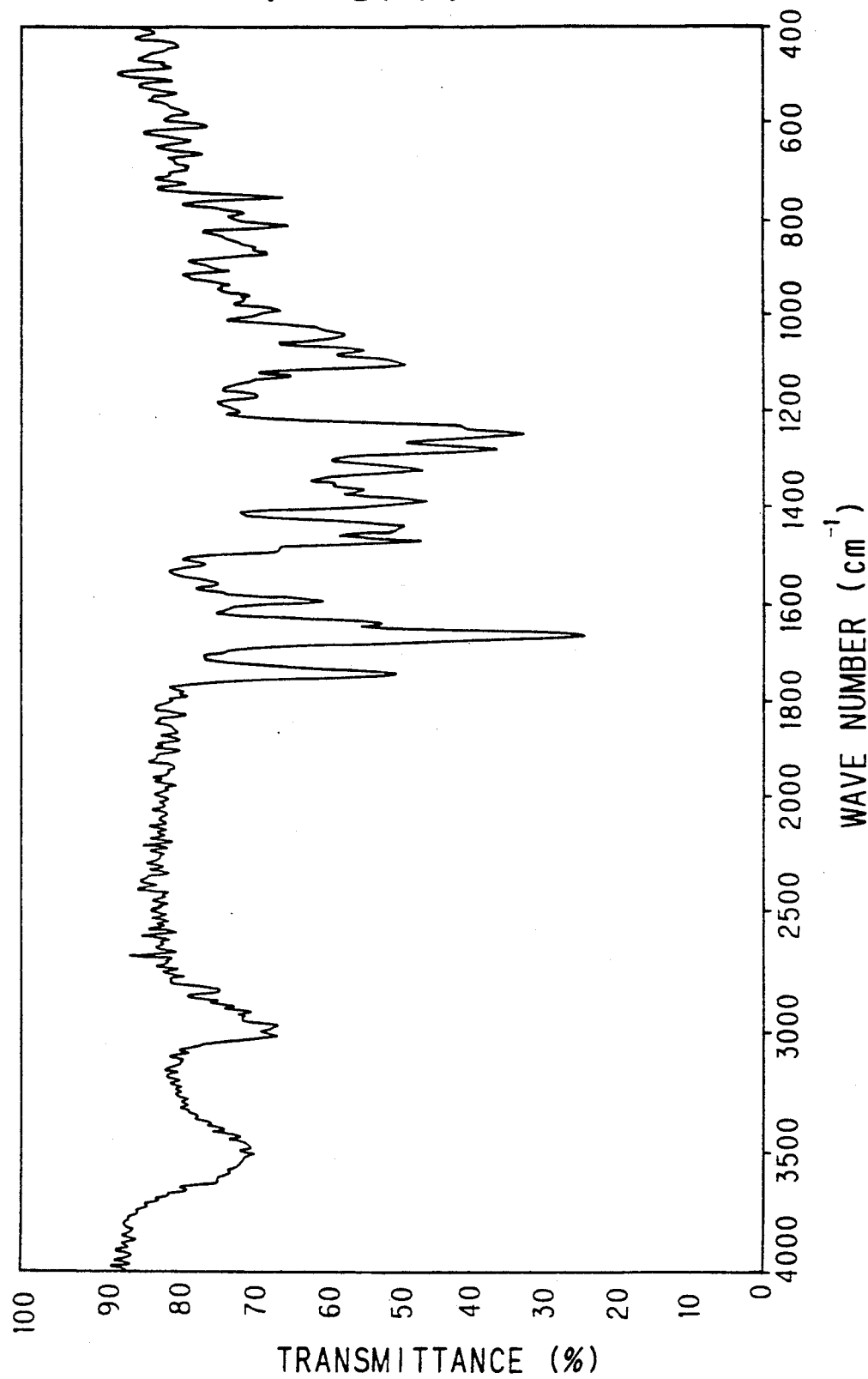
FIG. 17 is an infrared absorption spectrum of HP530H with a potassium bromide tablet.

(e) Infrared absorption spectrum: The spectrum measured using a potassium bromide tablet is shown in FIG. 17.

Figure 18:
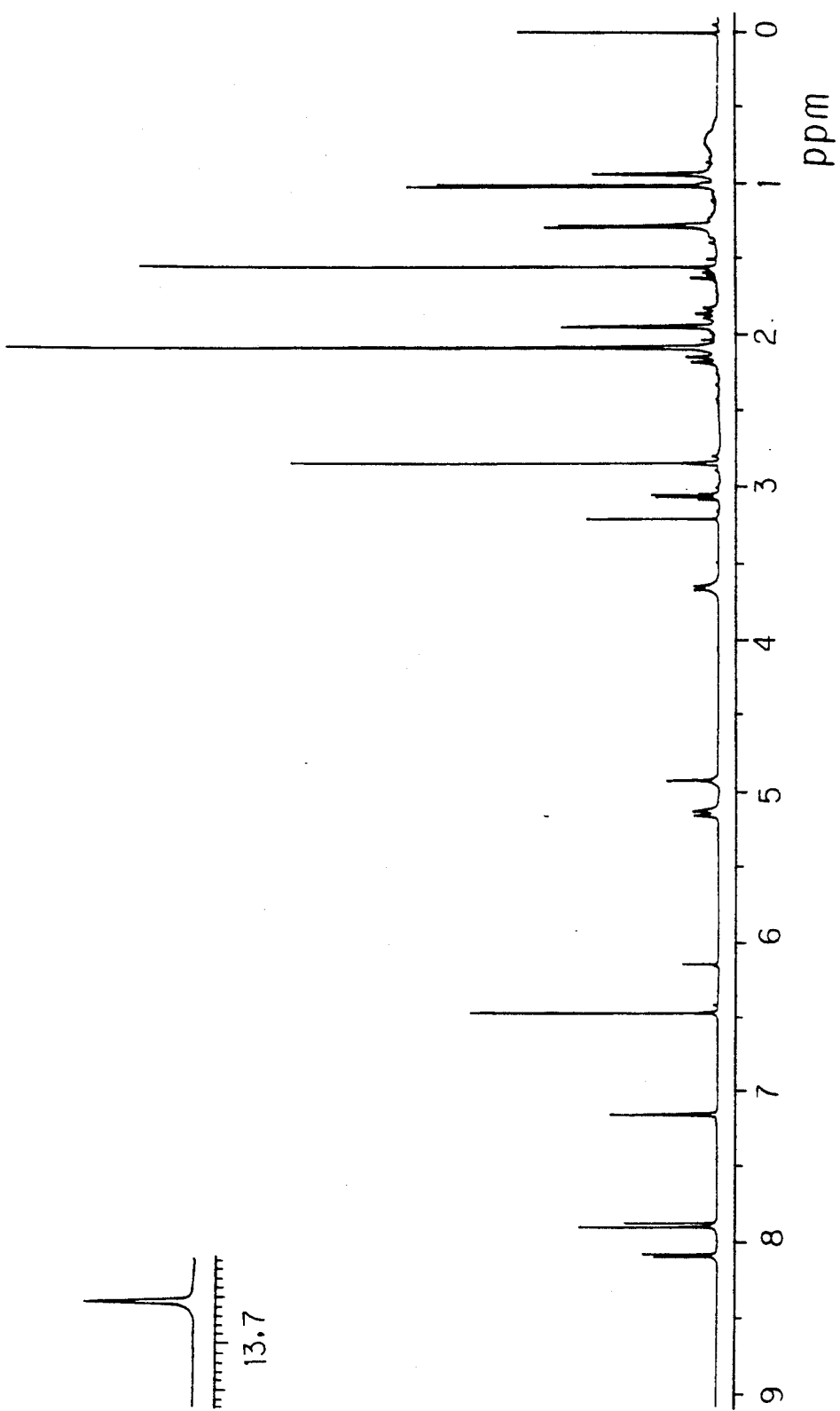
FIG. 18 is a $^1$H-nuclear magnetic resonance spectrum of HP530H in a deutero benzene solution with tetramethylsilane (TMS) being an internal reference.

(f) $^1$H-nuclear magnetic resonance spectrum: The 400 MHz $^1$H-NMR spectrum measured in deutero benzene is shown in FIG. 18.

(g) $^{13}$C-nuclear magnetic resonance spectrum: The 100 MHz $^{13}$C-NMR spectrum measured in deutero benzene is as follows. δ(ppm): 188.0(s), 181.2(s), 178.3(s), 170.3(s), 167.7(s), 158.9(s), 156.3(s), 149.8(s), 139.9(s), 136.2(s), 133.8(d), 131.3(s), 126.6(s), 125.8(d), 119.9(s), 119.3(d), 116.4(s), 109.7(d), 72.0(d), 71.7(d), 70.4(d), 63.6(s), 61.5(d), 57.3(s), 38.2(t), 37.5(q), 37.5(q), 24.0(q), 20.9(q), 18.2(q), 13.7(q), 13.5(q), 11.7(q)

(h) Solubility:

Soluble in acidic water, methanol and chloroform, hardly soluble in ethyl acetate, acetone and n-hexane and insoluble in water (i) Color reactions: Positive to Dragendorff reagent and vanillin sulfate (j) Basic, neutral and acidic distinction: Basic (k) Appearance: Yellow amorphous powder

EXAMPLE 10

Forty-five liters (45 l) of the culture filtrate obtained in Example 9 was extracted by 45 l of ethyl acetate and the resulting ethyl acetate layer was concentrated under a reduced pressure to give 450 ml of a solution containing HP530H. Thereafter the procedures were carried out in the same manner as in Example 9 and 1.0 mg of yellow powder of pure HP530H was obtained.

The physico-chemical properties of this compound were the same as those of the compound obtained in Example 9.

EXAMPLE 11

In 1.0 ml of pyridine was dissolved 9.2 mg of HP530D, and 0.2 ml of propionic anhydride was added to the solution under ice-cooling. The reaction mixture was stirred at room temperature for 48 hours, and then poured into 10 ml of ice-water. The aqueous solution was extracted twice with 20 ml of chloroform. The separated chloroform layer was washed with 50 ml of water, followed by 50 ml of a saturated sodium chloride aqueous solution, and then dried over anhydrous sodium sulfate overnight. The chloroform solution, after removal of sodium sulfate by filtration, was concentrated under reduced pressure to yield a yellow oily substance.

The oily substance dissolved in small amounts of chloroform was charged on a silica gel preparative thin layer plate (silica gel 60, $F_{254s}$, No. 13794, a product of Merck Co.) and then developed by the solvent system of chloroform-methanol (50:1). A reaction product was eluted from the silica gel removed from the plate by 50 ml of chloroform. The resulting chloroform solution, washed by 50 ml of a saturated sodium hydrogen carbonate aqueous solution and separated, was evaporated under reduced pressure to obtain 5.0 mg of 11-O-propionyl HP530D. The physico-chemical properties of this compound are tabulated below.

11-O-propionyl HP530D (a) Molecular weight and Molecular formula: 671, $C_{38}H_{41}NO_{10}$ (b) Mass spectrum (FAB-MS/Pos.): $(M+H)^+$ m/z 672

(c) Specific rotation $[\alpha]_D^{20} = +101.7°$ (c=0.1, chloroform)

(d) Ultraviolet absorption spectrum: $\lambda_{max}^{MeOH}$ nm ($\epsilon$) 240(32,800), 263(27,900), 361(7,100)

(e) Infrared absorption spectrum $\nu_{max}^{KBr}$ cm$^{-1}$: 2940, 1775, 1750, 1685, 1665, 1600

(f) $^1$H nuclear magnetic resonance spectrum: The 400 MHz $^1$H-NMR spectrum measured in deuterio chloroform with TMS being the reference is as follows:
CDCl$_3$ $\delta$(ppm) 8.22(1H,d), 8.06(1H,d), 8.01(1H,s), 6.48 (1H, s), 6.03(1H, dq), 5.40(1H, dd), 5.32(1H, br), 5.21(1H, d), 4.31(1H, dq), 4.08(1H, d), 2.99(3H, s), 2.82(2H, q), 2.28(6H, s), 2.19(3H, s), 1.88(3H, d), 1.80(3H, s), 1.41(3H, d), 1.38(3H, t), 1.02(3H, s)

(g) Color reactions: Positive to Dragendorff reagent and vanillin sulfate (h) Thin-layer chromatography: The sample was developed with chloroform methanol (50:1) on silica gel thin-layer plate (Merck Art. 5715). Rf value was 0.42

(i) Appearance: Yellow amorphous powder

EXAMPLE 12

11.0 mg of HP530D was dissolved in 20 ml of methanol and stirred at room temperature for 48 hours. The methanol solution was concentrated under reduced pressure to give deacetyl HP530D quantitatively. The resulting deacetyl HP530D was dissolved in 1.0 ml of pyridine, and 0.2 ml of propionic anhydride was added to the solution under ice-cooling. The reaction mixture was stirred at room temperature for 48 hours, and then poured into 10 ml of ice-water. The aqueous solution was extracted twice with 20 ml of chloroform. The separated chloroform layer was washed with 50 ml water, followed by 50 ml of a saturated sodium chloride aqueous solution, and then dried over anhydrous sodium sulfate over night. The chloroform solution, after removal of sodium sulfate by filtration, was concentrated under reduced pressure to yield a yellow oily substance.

The oily substance dissolved in small amounts of chloroform was charged on a silica gel preparative thin layer plate (Silica Gel 60, $F_{254s}$, No. 13794, a product of Merck Co.) and then developed by the solvent system of chloroform-methanol (50:1). A reaction product was eluted from the silica gel removed from the plate by 50 ml of chloroform. The resulting chloroform solution, washed by 50 ml of a saturated sodium hydrogen carbonate aqueous solution and separated, was evapolated under reduced pressure to obtain 7.3 mg of deacetyl-3', 11-O-dipropionyl HP530D.

The physico-chemical properties of this compound are tabulated below.

Deacetyl-3', 11-O-dipropionyl HP530D (a) Molecular weight and Molecular formula: 685, $C_{39}H_{43}NO_{10}$ (b) Mass spectrum (FAB-MS/Pos.): $(M+H)^+$ m/z 686

(c) Specific rotation: $[\alpha]_D^{20} = +110.7°$ (c=0.1, chloroform)

(d) Ultraviolet absorption spectrum:
$\lambda_{max}^{MeOH}$ nm ($\epsilon$): 240(36,900), 263(31,300), 360(7,800)

(e) Infrared absorption spectrum: $\nu_{max}^{KBr}$ cm$^{-1}$: 2960, 1790, 1755, 1695, 1675, 1605

(f) $^1$H nuclear magnetic resonance spectrum The 400 MHz $^1$H-NMR spectrum measured in deuterio chloroform with TMS being the reference is as follows:
CDCl$_3$: $\delta$(ppm) 8.22(1H,d), 8.08(1H,d), 8.01(1H,s), 6.49 (1H, s), 6.03(1H, dq), 5.38(1H, dd), 5.32(1H, br), 5.23(1H, d), 4.31(1H, dq), 4.08(1H, d), 3.00(3H, s), 2.82(2H, br.q), 2.48(2H, q), 2.28(6H, s), 1.88(3H, d), 1.80(3H, s), 1.42(3H, d), 1.37(3H, t), 1.23(3H, t), 1.01(3H, s)

(g) Color reactions: Positive to Dragendorff reagent and vanillin sulfate (h) Thin-layer chromatography: The sample was developed with chloroform-methanol (50:1) on silica gel thin-layer plate (Merck Art. 5715). Rf value was 0.48

(i) Appearance: Yellow amorphous powder

EXAMPLE 13

In 1.0 ml of pyridine was dissolved 8.6 mg of HP530D, and 0.2 ml of n-butyric anhydride was added to the solution under ice-cooling. The reaction mixture was stirred at room temperature for 48 hours, and then poured into 10 ml of ice-water. The aqueous solution was extracted twice with 20 ml of chloroform. The separated chloroform layer was washed with 50 ml of water, followed by 50 ml of a saturated sodium chloride aqueous solution, and then dried over anhydrous sodium sulfate over night. The chloroform solution, after removal of sodium sulfate by filtration, was concentrated under reduced pressure to yield a yellow oily substance.

The oily substance dissolved in small amounts of chloroform was charged on a silica gel preparative thin layer plate (silica gel 60, $F_{254s}$, No. 13794, a product of Merck Co.) and then developed by the solvent system of chloroform-methanol (50:1). A reaction product was eluted from the silica gel removed from the plate by 50 ml of chloroform. The resulting chloroform solution, washed by 50 ml of a saturated sodium hydrogen carbonate aqueous solution and separated, was evapolated under reduced pressure to obtain 5.4 mg of 11-O-butyryl HP530D The physico-chemical properties of this compound are tabulated below.

11-O-butyryl HP530D (a) Molecular weight and Molecular formula: 685, $C_{39}H_{43}NO_{10}$ (b) Mass spectrum (FAB-MS/Pos.): $(M+H)^+ m/z$ 686

(c) Specific rotation: $[\alpha]_D^{20} = +94.8°$ (c=0.1, chloroform)

(d) Ultraviolet absorption spectrum: $\lambda_{max}^{MeOH}$ nm ($\epsilon$): 238(40,400), 260(sh 35,500), 358(8,900)

(e) Infrared absorption spectrum:
$\nu_{max}^{KBr}$ cm$^{-1}$: 2930, 1770, 1745, 1680, 1655, 1590

(f) $^1$H nuclear magnetic resonance spectrum The 400 MHz $^1$H-NMR spectrum measured in deuterio chloroform with TMS being the reference is as follows: CDCl$_3$: $\delta$(ppm) 8.22(1H,d), 8.05(1H,d), 8.00(1H,s), 6.48(1H, s), 6.02(1H, dq), 5.38(1H, dd), 5.30(1H, br.), 5.22(1H, d), 4.30(1H, dq), 4.07(1H, d), 3.00(3H, s), 2.79(2H, br.), 2.28(6H, s), 2.18(3H, s), 1.90(2H, tq), 1.87(3H, d), 1.80(3H, s), 1.41(3H, d), 1.10(3H, t), 1.01(3H, s)

(g) Color reactions:
Positive to Dragendorff reagent and vanillin sulfate (h) Thin-layer chromatography:
The sample was developed with chloroform-methanol (50:1) on silica gel thin-layer plate (Merck Art. 5715). Rf value was 0.45.

(i) Appearance: Yellow amorphous powder

EXAMPLE 14

9.2 mg of HP530D was dissolved in 20 ml of methanol and stirred at room temperature for 48 hours. The methanol solution was concentrated under reduced pressure to give deacetyl HP530D quantitatively The resulting deacetyl HP530D compound was dissolved in 1.0 ml of pyridine, and 0.2 ml of n-butyric anhydride was added to the solution under ice-cooling. The reaction mixture was stirred at room temperature for 48 hours, and then poured into 10 ml of ice-water. The aqueous solution was extracted twice with 20 ml of chloroform. The separated chloroform layer was washed with 50 ml water, followed by 50 ml of a saturated sodium chloride aqueous solution, and then dried over anhydrous sodium sulfate over night. The chloroform solution, after removal of sodium sulfate by filtration, was concentrated under reduced pressure to yield a yellow oily substance.

The oily substance dissolved in small amounts of chloroform was charged on a silica gel preparative thin layer plate (Silica gel 60, F$_{254s}$, No. 13794, a product of Merck Co.) and then developed by the solvent system of chloroform-methanol (50:1). A reaction product was eluted from the silica gel removed from the plate by 50 ml of chloroform. The resulting chloroform solution, washed by 50 ml of a saturated sodium hydrogen carbonate aqueous solution and separated, was evapolated under reduced pressure to obtain 6.4 mg of deacetyl-3', 11-O-dibutyryl HP530D. The physico-chemical properties of this compound are tabulated below.

Deacetyl-3',11-O-dibutyryl HP530D:

(a) Molecular weight and Molecular formula: 713, $C_{41}H_{47}NO_{10}$ (b) Mass spectrum (FAB-MS/Pos.): $(M+H)^{30}$ m/z 714

(c) Specific rotation: $[\alpha]_D^{20}= +80.2°$ (c=0.1, chloroform)

(d) Ultraviolet absorption spectrum: $\lambda_{max}^{MeOH}$ nm ($\epsilon$): 238(32,000), 260(sh 31,700), 360(6,900)

(e) Infrared absorption spectrum: $\nu_{max}^{KBr}$ cm$^{31}$ $^1$: 2930, 1775, 1740, 1680, 1660, 1590

(f) $^1$H nuclear magnetic resonance spectrum: The 400 MHz $^1$H-NMR spectrum measured in deuterio chloroform with TMS being the reference is as follows: CDCL$_3$: $\delta$(ppm) 8.22 (1H, d), 8.06(1H,d), 8.01(1H,s), 6.48(1H,s), 6.03($^1$H, dq), 5.38($^1$H, dd), 5.32($^1$H, br.), 5.24($^1$H, d), 4.29($^1$H, dq), 4.06($^1$H, d), 3.00(3H, s), 2.79(2H, br.), 2.40(2H, t), 2.26(6H, s), 1.89(2H, tq), 1.86(3H, d), 1.80(3H, s), 1.73(2H, tq), 1.40(3H, d), 1.09(3H, t), 1.01(3H, s), 1.00(3H, t)

(g) Color reactions: Positive to Dragendorff reagent and vanillin sulfate (h) Thin-layer chromatography: The sample was developed with chloroform-methanol (50:1) on silica gel thin-layer plate (Merck Art. 5715). Rf value was 0.61

(i) Appearance: Yellow amorphous powder

As described already, the HP530 compounds and their derivatives in accordance with the present invention exhibit the antimicrobial and antitumor activities and are therefore believed useful as antimicrobial and antitumor substances and particularly because of their strong antitumor activity, their application as the antitumor agent for chemotherapy is expected.

What is claimed is:

1. A HP530 compound of the formula (I):

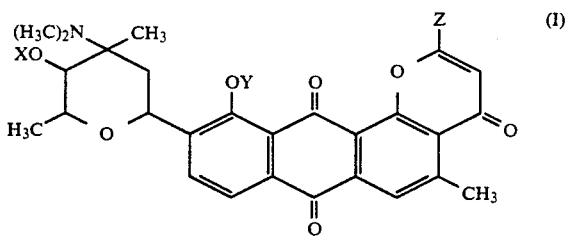

wherein X is a carboxylic acyl group of 2 to 4 carbon atoms or a hydrogen atom, Y is a carboxylic acyl group of 2 to 4 carbon atoms or a hydrogen atom and Z is a group expressed by the formula (II), (III) or (IV):

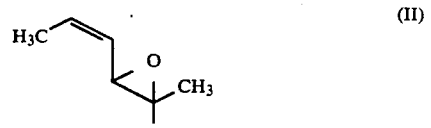

or a pharmaceutically acceptable salt thereof.

2. A HP530 compound of the formula (V):

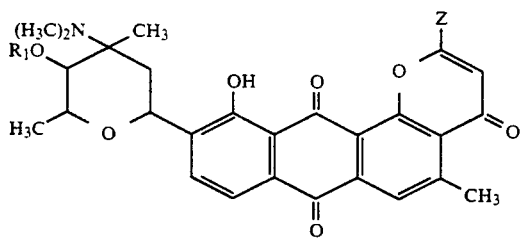

wherein R₁ is a carboxylic acyl group of 2 to 4 carbon atoms and Z is a group expressed by the formula (II), (III) or (IV):

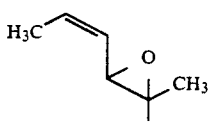

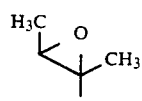

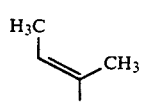

or a pharmaceutically acceptable salt thereof.

3. A HP530 compound of the formula (VI):

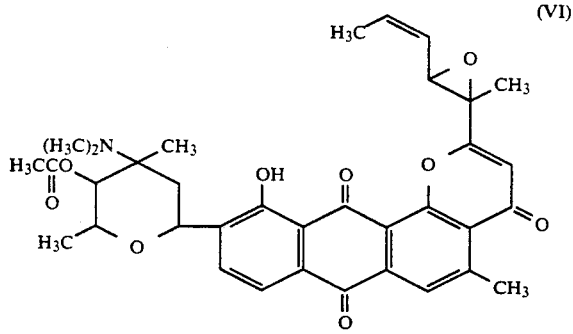

or a pharmaceutically acceptable salt thereof.

4. A HP530 compound of the formula (IX):

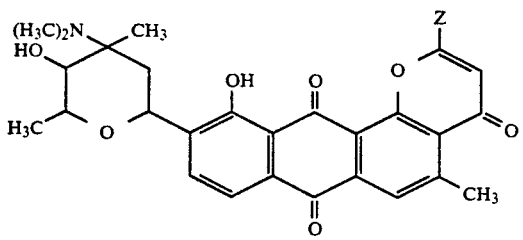

wherein Z is a group expressed by the formula (II), (III) or (IV):

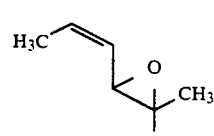

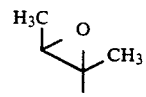

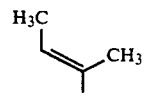

or pharmaceutically acceptable salt thereof.

5. A HP530 compound of the formula (X):

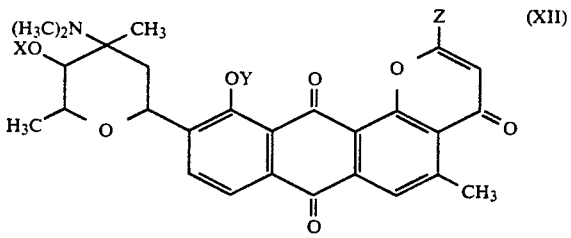

or a pharmaceutically acceptable salt thereof.

6. A HP530 compound of the Formula (XII):

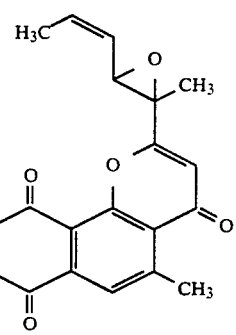

wherein X is carboxylic acyl group of 2 to 4 carbon atoms or a hydrogen atom, Y is a carboxylic acyl group of 2 to 4 carbon atoms or a hydrogen atom, and Z is a group expressed by the Formula (II), (III) or (IV):

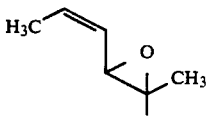

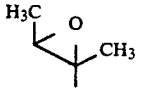

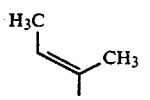

except when X is an acetyl group, Y is not hydrogen, or a pharmaceutically acceptable salt thereof.

7. HP530E expressed by the following formula (VII) or its pharmaceutically permissible salts:

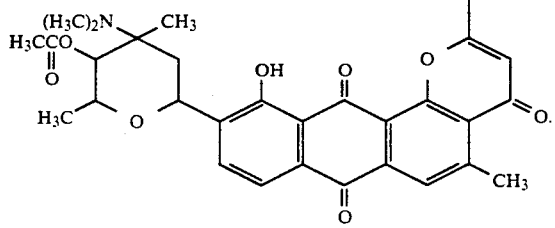

8. HP530G expressed by the following formula (VIII) or its pharmaceutically permissible salts:

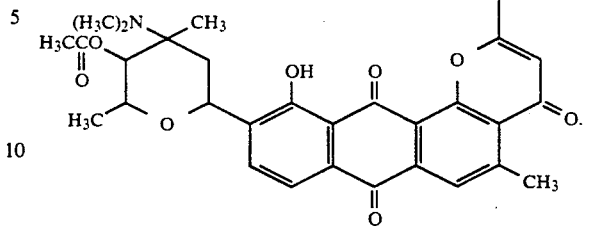

9. Deacetyl HP530E expressed by the following general formula (XI) or its pharmaceutically permissible salts:

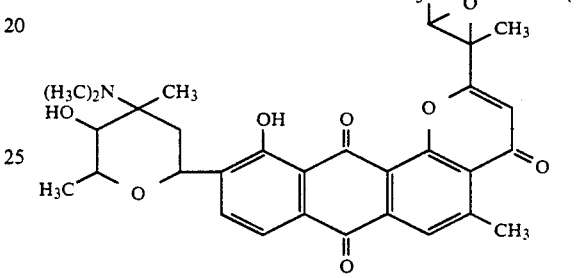

10. An antitumor substance comprising a HP530 compound of claim 1 as an active ingredient and a pharmaceutically acceptable carrier.

* * * * *

UNITED STATES PATENT AND TRADEMARK OFFICE
CERTIFICATE OF CORRECTION

PATENT NO. : 5,168,100

DATED : DECEMBER 1, 1992

INVENTOR(S) : NAOKI ABE ET AL

It is certified that error appears in the above-identified patent and that said Letters Patent is hereby corrected as shown below:

Column 1, line 26, "compounds(Japanese" should read --compounds (Japanese--.

Column 1, line 49, "H-nucleare magnetic" should read --H-nuclear magnetic--.

Column 4, line 56, "characteristics" should read --characteristics:--.

Column 5, line 39, "Cell wall type" should read --Cell wall type:--;
        line 63, "F.R. I." should read --F.R.I.--.

Column 7, line 8, "the invention is" should read --the invention are--;
        line 12, "following methods In" should read --following methods. In--;
        line 28, "solution Alternatively" should read --solution. Alternatively--;
        line 32, "solution Examples" should read --solution. Examples--;

UNITED STATES PATENT AND TRADEMARK OFFICE
CERTIFICATE OF CORRECTION

PATENT NO. : 5,168,100
DATED : DECEMBER 1, 1992
INVENTOR(S) : NAOKI ABE ET AL

It is certified that error appears in the above-identified patent and that said Letters Patent is hereby corrected as shown below:

Column 7, line 40, "and the like Recovery" should read --and the like. Recovery--.

Column 8, line 31, "derivatives the present" should read --derivatives of the present--.

Column 9, line 29, "extremelly low" should read --extremely low--.

Column 10, line 3, "salt solution Examples" should read --salt solution. Examples--;
line 38, "charged Streptomyces" should read --charged. Streptomyces--;
line 40, "flask Shaking" should read --flask. Shaking--;
line 43, "culture The primary" should read --culture. The primary--;
line 47, "finally 30%" should read --finally 3%--.

Column 11, line 43, "spectrum The" should read --spectrum: The--.

UNITED STATES PATENT AND TRADEMARK OFFICE
CERTIFICATE OF CORRECTION

PATENT NO. : 5,168,100
DATED : DECEMBER 1, 1992
INVENTOR(S) : NAOKI ABE ET AL

It is certified that error appears in the above-identified patent and that said Letters Patent is hereby corrected as shown below:

Column 12, line 15, "sp. HP530 BP-2786)" should read --sp. HP530 (FERM BP-2786)--;

line 31, "acetone After" should read --acetone. After--.

Column 13, line 17, "absorption spectrum The" should read --absorption spectrum. The--;

line 21, "resonance spectrum The" should read --resonance spectrum: The--;

line 25, "resonance spectrum The" should read --resonance spectrum: The--;

line 34, "Solubility Soluble" should read --Solubility: Soluble--;

line 43, "liters (45 () of" should read --liters (45 l) of--;

line 47, "the procedures" should read --the procedure--;

line 61, "medium Streptomyces" should read --medium. Streptomyces--;

line 63, "flask Shaking" should read --flask. Shaking--;

UNITED STATES PATENT AND TRADEMARK OFFICE
CERTIFICATE OF CORRECTION

PATENT NO. : 5,168,100

DATED : DECEMBER 1, 1992

INVENTOR(S) : NAOKI ABE ET AL

It is certified that error appears in the above-identified patent and that said Letters Patent is hereby corrected as shown below:

Column 13, line 67, medium Shaking" should read --medium. Shaking--.

Column 14, line 13, "solution Acetone" should read --solution. Acetone--;
    line 29, "Furthermore.," should read --Furthermore,--;
    line 33, "named Among" should read --named. Among--;
    line 45, "precipitate yielded" should read --precipitate yielded.--;
    line 50, "below Cytotoxicity" should read --below. Cytotoxicity--;
    line 52, "HP530G" should read --HP530G:--;
    line 54, "molecular formula 573" should read --molecular formula: 573--.

Column 15, line 22, "Hundred-and-eighty" should read --One-hundred-and-eighty--;
    line 38, "48 hours Methanol" should read --48 hours. Methanol--;

UNITED STATES PATENT AND TRADEMARK OFFICE
CERTIFICATE OF CORRECTION

PATENT NO. : 5,168,100
DATED : DECEMBER 1, 1994
INVENTOR(S) : NAOKI ABE ET AL

It is certified that error appears in the above-identified patent and that said Letters Patent is hereby corrected as shown below:

Column 15, line 68, "1 ml/min" should read --1 ml/min.--.

Column 16, line 1, "absorption spectrum The" should read --absorption spectrum: The--;
    line 3, "absorption spectrum The" should read --absorption spectrum: The--;
    line 6, "resonance spectrum The" should read --resonance spectrum: The--;
    line 9, "resonance spectrum The" should read --resonance spectrum: The--;
    line 13, "149 6(s)" should read --149.6(s)--;
    line 37, "by a the system" should read --by a system--;
    line 66, "resonance spectrum The" should read --resonance spectrum: The--.

Column 17, line 1, "resonance spectrum The" should read --resonance spectrum: The--;
    line 41, "10 ( of 80% acetone" should read --10 l of 80% acetone.--;

UNITED STATES PATENT AND TRADEMARK OFFICE
CERTIFICATE OF CORRECTION

PATENT NO. : 5,168,100

DATED : DECEMBER 1, 1992

INVENTOR(S) : NAOKI ABE ET AL

It is certified that error appears in the above-identified patent and that said Letters Patent is hereby corrected as shown below:

Column 17, line 44, "solution Acetone" should read --solution. Acetone--;
    line 49 "sodium sulfate was" should read --sodium sulfate and was--;
    line 61, "carried out In" should read --carried out. In--.

Column 18, line 19, "liquid chromatography Elution" should read --liquid chromatography: Elution--;
    line 24, "absorption spectrum The" should read --absorption spectrum: The--.

Column 19, line 26, "Specific rotation" should read --Specific rotation:--.
    line 27, "nm ($\epsilon$)" should read --nm ($\epsilon$):--;
    line 30, "absorption spectrum $v_{max}^{KBr}$ cm$^{31}$" should read --absorption spectrum: $v_{max}^{KBr}$ cm$^{-1}$--;
    line 35, "CDCl$_3$" should read --CDCl$_3$:--;
    line 43, "with chloroform methanol" should read --with chloroform-methanol--.

UNITED STATES PATENT AND TRADEMARK OFFICE
CERTIFICATE OF CORRECTION

PATENT NO. : 5,168,100
DATED : DECEMBER 1, 1992
INVENTOR(S) : NAOKI ABE ET AL

It is certified that error appears in the above-identified patent and that said Letters Patent is hereby corrected as shown below:

Column 20, line 24, "resonance spectrum The" should read --resonance spectrum: The--;

line 67, "HP530D The" should read --HP530D. The--.

Column 21, line 12, "spectrum The" should read --spectrum. The--;

line 34, "quantitatively The" should read --quantitatively. The--;

line 67, "rotation: $[\alpha_D^{20}$" should read --rotation: $[\alpha_{JD}^{20}$--.

Column 22, line 4, "$cm^{31\ 1}$:" should read --$cm^{-1}$:--.

Signed and Sealed this

Twenty-eight Day of March, 1995

Attest:

BRUCE LEHMAN

*Attesting Officer*    *Commissioner of Patents and Trademarks*